(12) United States Patent
Masuo

(10) Patent No.: US 6,321,112 B1
(45) Date of Patent: Nov. 20, 2001

(54) DEVICE TO PROVIDE DATA AS A GUIDE TO HEALTH MANAGEMENT

(75) Inventor: Yoshihisa Masuo, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/340,940

(22) Filed: Jun. 28, 1999

(30) Foreign Application Priority Data

| Aug. 12, 1993 | (JP) | 5-200688 |
| Aug. 19, 1993 | (JP) | 5-213954 |
| Sep. 14, 1993 | (JP) | 5-299089 |

(51) Int. Cl.⁷ .................................................. A61B 5/05
(52) U.S. Cl. ............................................................. 600/547
(58) Field of Search ................................. 600/372, 547, 600/382; 702/19

(56) References Cited

U.S. PATENT DOCUMENTS

| 4,557,271 | 12/1985 | Stoller et al. . |
| 4,895,163 | 1/1990 | Libke et al. . |
| 4,947,862 | 8/1990 | Kelly . |
| 4,949,727 | 8/1990 | Yamazaki et al. . |
| 5,458,117 | 10/1995 | Chamoun et al. . |

*Primary Examiner*—George Manuel
(74) *Attorney, Agent, or Firm*—Morrison & Foerster LLP

(57) ABSTRACT

A high-frequency signal generator generates a signal passing from the subcutaneous fat layer toward both the deep and shallow tissue areas. A second high-frequency signal generator generates a signal that passes primarily toward the deeper tissue. Frequency switch unit is used to select a signal of one of the frequencies. This signal is applied across whichever two of electrodes are selected by electrode switch unit 32a. The impedance across the two limbs in contact with those electrodes is measured using the electrical potential derived at whichever two of the electrodes have been selected. From the impedance values and personal data such as weight and height, the visceral fat mass, visceral-to-subcutaneous fat ratio and other useful indicators are calculated.

11 Claims, 23 Drawing Sheets

FIG. 2
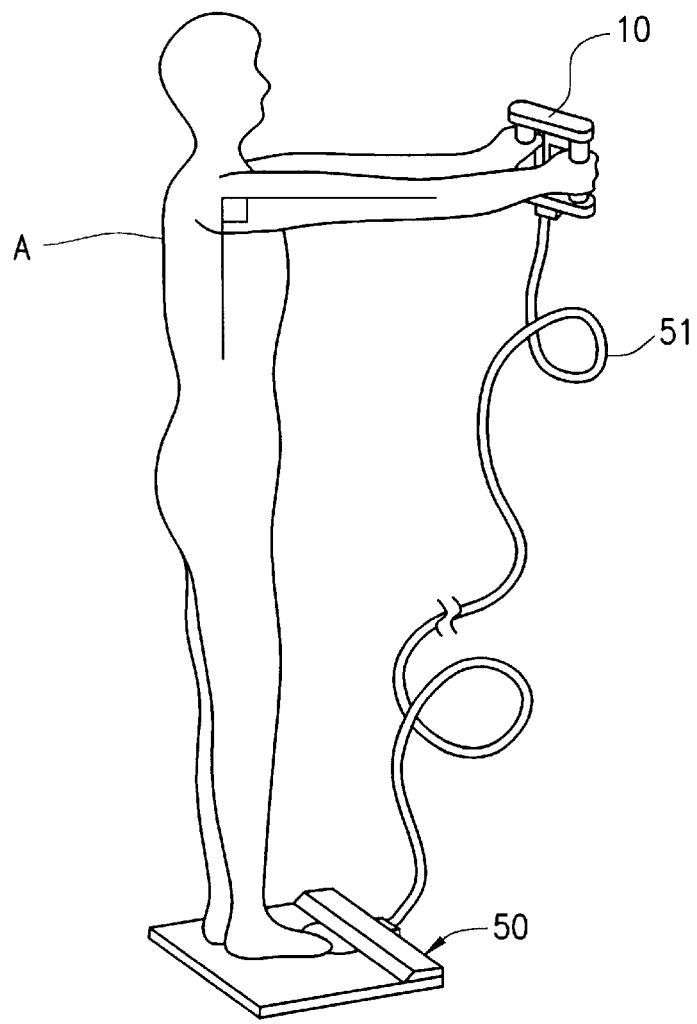
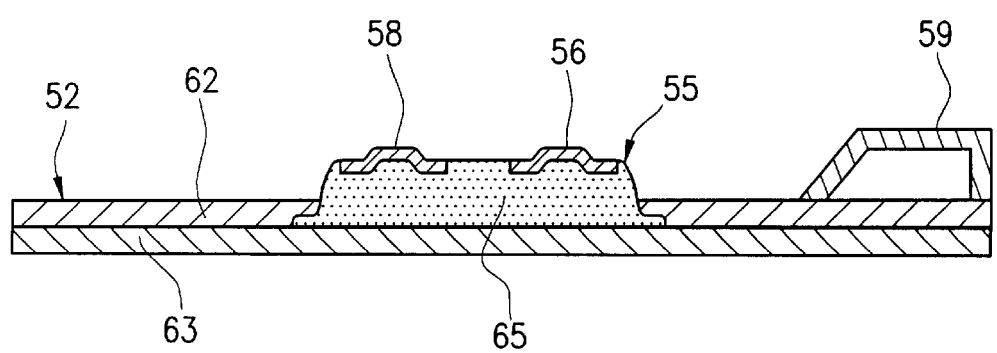
FIG. 3

DEVICE TO PROVIDE DATA AS A GUIDE TO HEALTH MANAGEMENT

FIELD OF THE INVENTION

This invention concerns a device and method to provide data about fat content of a human body as a guide to health management. More specifically, a technique of determining such values as total internal body fat, nonfat body mass, ratio of body fat, water mass, and basic metabolic rate are described. The present invention also describes calculating the visceral fat mass and the ratio of visceral-to-subcutaneous fat. Based on the results of these calculations, the device provides data to be used as a guide for health management.

BACKGROUND AND SUMMARY OF THE INVENTION

It is know to use four electrodes to measure the internal impedance of the body to determine a quantity related to internal body fat. This known scheme for measuring internal impedance is pictured in FIG. 24. The equipment includes a measuring device 1 connected to electrodes 2 and 3 by lead wires 6, and which apply a high-frequency signal; and electrodes 4 and 5, which measure the resistance of the body. The patient is made to lie on a bed, electrodes 2 and 3 are attached to the patient's right hand and right foot, and electrodes 4 and 5, which measure the resistance of the body, are attached to the right hand and foot close to electrodes 2 and 3, respectively. A high-frequency signal is applied to electrodes 2 and 3 by device 1, causing a current to pass into the patient's body. The potential difference between electrodes 4 and 5 is measured, and the impedance of the patient's body can be obtained from this potential difference and the strength of the current which was passed.

The inventor has found that devices such as shown in FIG. 24 suffer from the following problems.

(1) To prevent errors resulting from variation in the path of the current, and to ensure that the measurement would be sufficiently accurate, the patient had to be lying down. The patient's feet had to be spread so that there was no danger that they would touch each other, and the hands had to be kept well away from the torso. (2) Because of the aforesaid restrictions on the patient, and because of the difficulty of attaching the electrodes and conducting the test, a special technician was needed. The patient could not perform the test without medical supervision, and hence the device was not suitable for use in the home. (3) Since this device is designed to be used for the treatment of a great number of patients, it has a large key input and display unit, a printer, an AC power supply, and other components. This makes the device large and unwieldy. (4) The use of numerous electrodes with their extension cables made preparation and cleanup difficult. (5) Just as with an ECG, a user had to apply a conductor such as keratin cream to the portion of the hands and feet where the electrodes were to be attached so as to minimize the effect of contact resistance. (6) In estimating body fat by measuring impedance, impedance data for the body are more important than those for the hands and feet. Between the points where it is measured in the existing scheme, however, the impedance of the hand and foot is considerably larger than that of the body. The impedance of joints is especially high. It is well known that disparities between small- and large-boned people and those with small joins exert profound effect on measurement results.

For example, here are some results of measuring the impedance at different parts of the body.

1) Male with thick limbs: Between right hand and right foot, 350 Ω; right arm, 150 Ω; right foot, 130 Ω; thoracic region, 70 Ω
2) Female with slender limbs: Between right hand and right foot, 675 Ω; right arm, 360 Ω; right foot, 240 Ω; thoracic region, 75 Ω
3) Wrist joint: 25 to 50 Ω level Furthermore, there are in general two types of obesity subcutaneous and visceral. Though two patients may be similarly overweight, the viscerally obese patient will be prone to suffer from irregularities of sugar metabolism, such as high blood sugar or high blood insulin, and of fat metabolism, such as high blood cholesterol. The percentage of visceral fat in total internal fat is a significant criterion which can indicate whether the obesity is of the subcutaneous or visceral variety. At present, the only way to perform this test is with a large, highly accurate and extremely expensive device such as an X ray CT or MRI scanner. There has been a demand for a device employing a much simpler measurement scheme.

This invention was developed in view of the inventors noting the problems discussed above. The objective of the present invention is to provide a device which can supply data that would be useful as a guide for home health management. The present invention allows the patient to easily be able to measure the impedance developed across the body. The device determines the amount and ratio of visceral fat and the type of obesity. It would be compact, light, and inexpensive, and the accuracy of its measurements would be high. An individual is able to use the device in the privacy of their own home.

The device to provide data as a guide to health management includes: 1) a portable main unit with grip area for the right and left hands, furnished on either end of the main unit, each of which has an electrode to apply a high-frequency signal and an electrode to measure the resistance of the body. A foot electrode unit is connected by a cable to the aforesaid main unit, and has electrodes to apply high-frequency signals and electrodes to measure the electrical potential developed across the body. The portable main unit mentioned above has a first high frequency generator that generates a high-frequency signal which passes through both the shallow part of the body (where subcutaneous fat is located) and the deeper part of body (where visceral fat is located). A second frequency generator generates high-frequency signal which passes mainly in the deeper part of the body. An electrode selecting device selects which two of the aforesaid pairs of electrodes will be used by a switching operation.

A frequency selecting device switches frequencies to select one of the aforesaid series of high-frequency signals, and it applies them between the first electrodes of the selected pairs. The impedance between the two pairs of electrodes from the electrical potential detected across the respective second electrode in each of the pairs is detected, and this is used to calculate the visceral fat mass based on the impedances measured when the two high-frequency signals are applied. Other specific physical data which have been entered independently, such as weight, can also be used.

The patient uses this device by grasping the grips with both hands so that each hand makes contact with the two electrodes in the grip. The user steps onto the stand, causing the sole of each foot to make contact with the two foot electrodes. By operating the device to switch electrodes and the device to switch frequencies, the user can easily measure the impedance between the various locations while in a standing position.

The portion of the impedance attributable to the limbs can be calculated by adding the value of the impedance between the feet ($Z_{2f}$) to the value of the impedance between the hands ($Z_{2h}$). These values are subtracted from the value of the impedance between hand and foot ($Z_{2b}$) to obtain the impedance value for the thoracic region alone ($Z_{2s}$). From this impedance data and specific physical data input by the patient, the visceral fat mass can be calculated:

$$Z_{2s} = Z_{2b} - (Z_{2h} + Z_{2f})/2$$

Another aspect of this application calculates, from the values for total body fat mass and visceral fat mass obtained by the device discussed above, a value for subcutaneous fat mass, and calculates the ratio of visceral-to-subcutaneous fat masses. From this ratio, the present invention allows a determination of whether the obesity is of the subcutaneous or visceral type.

Another aspect of this application provides elements including: 1) a portable main unit; 2) grips for the right and left hands, furnished on either end of the main unit, each of which has an first electrode to apply a high-frequency signal and an second electrode to measure the resistance of the body; 3) a foot electrode unit, connected by a cable to the aforesaid main unit, which has electrodes to apply high-frequency signals and electrodes to measure the electrical potential developed across the body.

The portable main unit mentioned above is equipped with the following: 1) a high frequency generator has a high-frequency signal which passes through both the shallow part of the body (where subcutaneous fat is located) and the deeper part of the body (where visceral fat is located), 2) an electrode selecting device including switches connected to establish connections that select any two of the aforesaid first and second electrodes; 3) an impedance measuring device to measure the impedance between the two pairs of electrodes from the electrical potential detected across the respective second electrode in each of the pairs; 4) a estimating device which estimates an waist-to-hip ratio based on the data concerning impedance between the two pairs of electrodes by the device for that purpose, and on specific physical data which have been entered independently; and 5) a calculating device to calculate visceral fat mass based on the waist-to-hip ratio which has been estimated.

This device can, for example, measure the impedance $Z_f$ between the patient's feet, the impedance $Z_h$ between the patient's hands, and/or the impedance $Z_b$ between hand and foot. From these values the impedance $Z_s$ of the thoracic region is obtained.

The device uses the impedance $Z_{fs}$ of the hip region, which is obtained from the hand-to-hand impedance $Z_h$ and the foot-to-foot impedance $Z_f$, and the impedance $Z_s$ of the thoracic region, to estimate a waist-to-hip ratio. It estimates the visceral fat mass and the visceral-to-subcutaneous fat ratio using this waist-to-hip ratio, the total body fat ratio, the converted fat and other values.

The present invention allows accurate measurement of body fat ratio and visceral fat mass. The measurement is not affected by differences in the density of patients' hands and feet. It provides, in a simple and reliable fashion, a measurement of visceral fat mass, which is a crucial datum in health management.

This device allows obtaining a value for the subcutaneous fat mass as well as the subcutaneous-to-visceral fat ratio. This allows an evaluation to be made as to whether the patient's obesity is of the subcutaneous or visceral variety.

This device uses the various measured impedance values to estimate a wastes/hip ratio, and from this estimated waist/hip ratio it calculates an estimate of body fat mass. From this it is able to obtain a value for visceral fat mass, a crucial datum in health management. Using the patient's waist/hip ratio to supplement the physical data, the device can provide, in a simple and reliable fashion, such critical values as the proportional index, the amount and ratio of visceral fat within the total fat mass, and whether the obesity is of the subcutaneous or visceral variety.

BRIEF DESCRIPTION OF THE DRAWINGS

These and other aspects of the invention will now be described in detail with reference to the accompanying drawings, wherein:

FIG. 2 illustrates the use of that same device;

FIG. 3 is a cross section of the foot electrode unit of the same device, taken on line A—A in FIG. 1;

DETAILED DESCRIPTION OF THE EMBODIMENT

Figure 1:
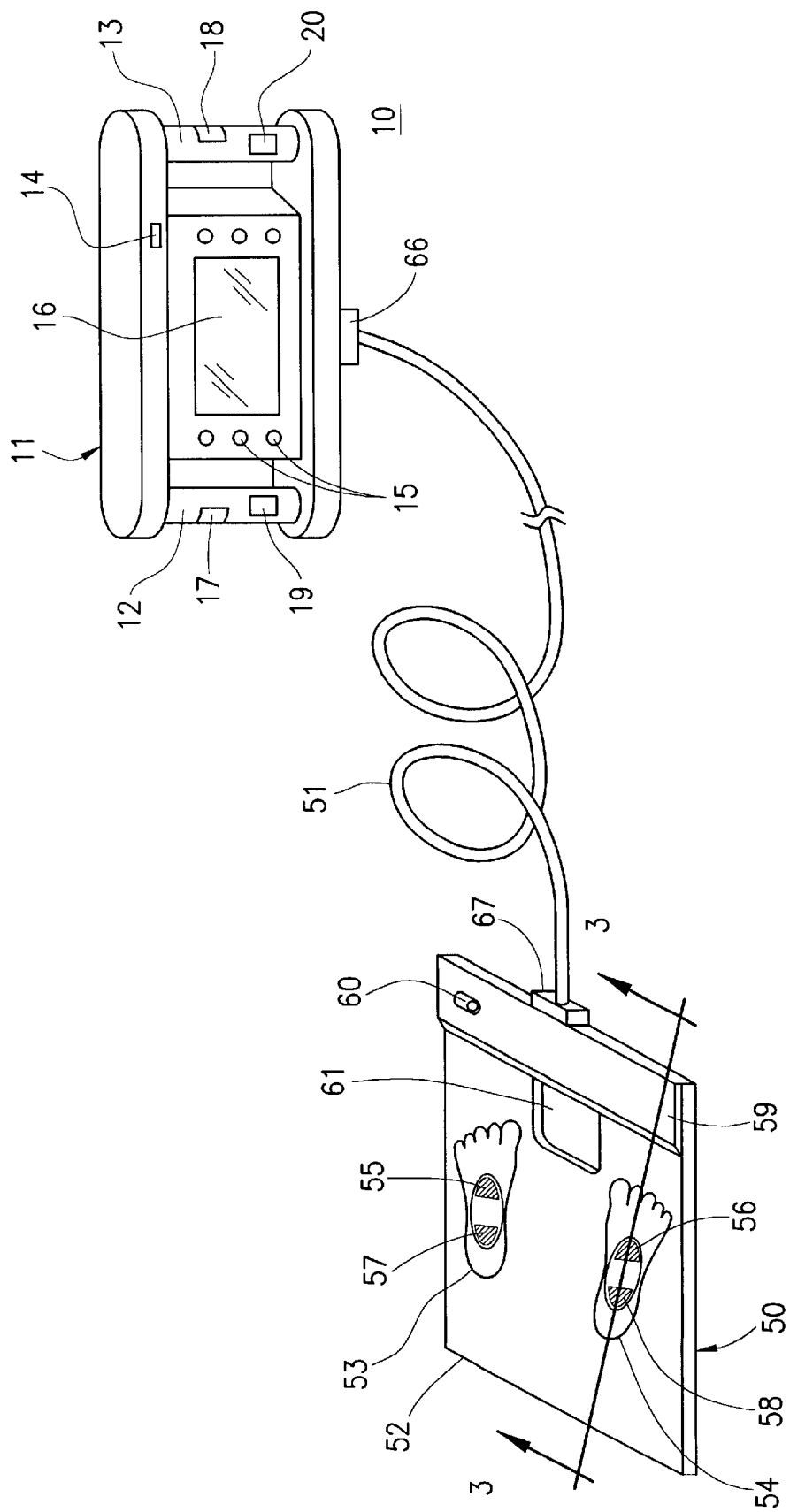
FIG. 1 is a perspective view of the exterior of a device to provide data as a guide to health management which is an ideal embodiment of this invention.

FIG. 1 is a perspective view of the exterior of a device to provide data as a guide to health management. The device of this embodiment includes main unit 10, foot electrode unit 50, and cable 51, which connects unit 10 to unit 50.

Main unit 10 has body 11 having left and right grips 12 and 13 formed integrally on either side of body 11. The front of body 11 includes power supply switch 14; key switches 15 which are used to enter the start command and physical characteristics of the patient such as height and weight; and display 16, which displays the measurement results and advisory data. Display 16 is located in the center of an area between left and right handgrips 12 and 13.

Left and right grips 12 and 13 include vertical cylinders on whose surfaces are provided electrodes 17 and 18 between which is applied a high-frequency signal, and electrodes 19 and 20 (see FIG. 4), which measure the resistance of the body.

Foot electrode unit 50 includes flat rectangular sheet 52, on which are two position guides, including guide 53 for the left foot and guide 54 for the right foot. Each of these guides has two electrodes. A high-frequency signal is applied between electrodes 55 and 56. The resistance of the body is measured between electrodes 57 and 58. The top surface of the front end of sheet 52 is partially covered by housing 59. Display 60, which is used to monitor the state of the measurement, is seated in this housing. Opening 61 is located toward the front end of sheet 52 and between the foot position guides.

FIG. 3 shows a cross section along the Line A—A in FIG. 1. Sheet 52 is constructed of surface layer 62 and underlayer 63. Layers 62 and 63 can be composed of PVC, PET, polyethylene, or some similar substance. Elastic protrusion 65 is located in the region corresponding to the arch of the foot, in position guide 54. The two electrodes 56 and 58 are formed on elastic protrusion 65. FIG. 3 shows a cross section of the position guide for the right foot; it should be understood that the guide for the left foot has an identical construction.

The electrodes are mounted on protrusions 64 and 65 to ensure that solid contact with the soles of the feet when the user's feet are placed in guides 53 and 54. Protrusions 64 and 65 are constructed of an elastic sheet made of a material such as silicon rubber. Housing 59 can be made of a material like ABS or PVC.

Cable 51 terminates in connectors 66 and 67 at respective ends thereof which allow connection to main unit 10 and foot electron unit 50 in such a way that it can easily be connected or disconnected. Let us consider how the device of this embodiment would be used to measure the impedance of the user's body. User A would stand as shown in FIG. 2, with both feet in guides 53 and 54 on electrode unit 50. The user would then grasp grip 12 on main unit 10 with the left hand and grip 13 with the right hand. Measurements are taken after stretching the arms forward horizontally so as to hold unit 10 chest-high.

Figure 4:
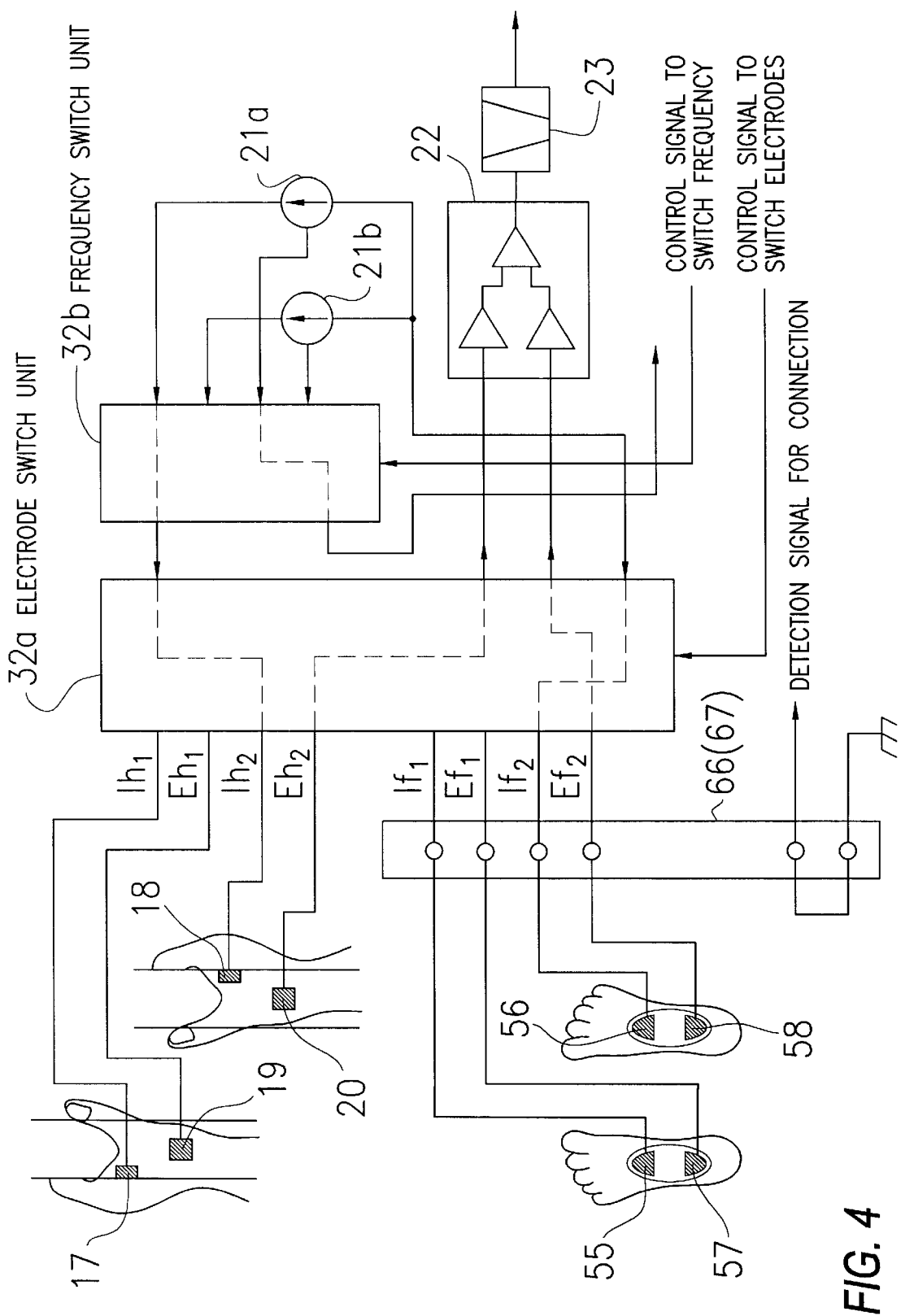
FIG. 4 is a block diagram showing a portion of the circuitry in the same device.
Figure 5:
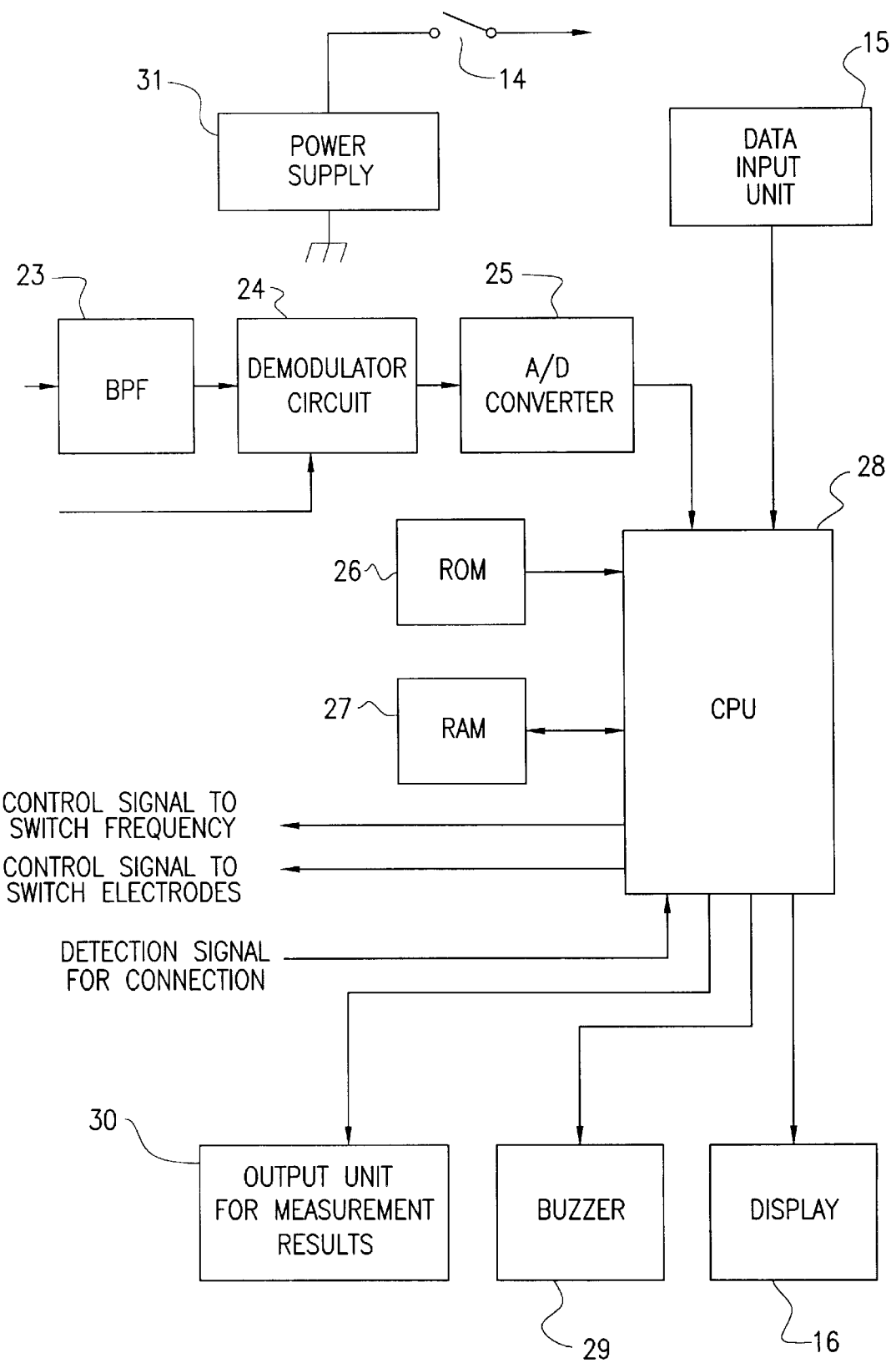
FIG. 5 is a block diagram which, together with FIG. 4, illustrates the structure of the circuits in the same embodiment.

FIGS. 4 and 5 show block diagrams of the controlling circuits for this embodiment.

The internal circuits of this device include frequency generating circuit 21a, which generates a constant-current high-frequency signal whose frequency $F_1=50$ KHZ (10 KHZ $<f_1<100$ KHZ). Another frequency generating circuit 21b generates another constant-current high-frequency signal whose frequency $f_2=100$ KHZ (40 KHZ$<f_2<$500 KHZ). Differential amplifier 22 receives the electrical potential signals from electrodes 19 and 20. The output of differential amplifier 22 is filtered through band pass filter 23, which filters out signals of frequencies other than frequency $f_0$. That output is demodulated by demodulator circuit 24, which demodulates the high-frequency signal component; then A/D converter 25 converts the analog signals into digital signals input to CPU 28. CPU 28 also has associated ROM 26 and RAM 27. CPU 28, which reads in the input from A/D converter 25 and the data from input unit 15, including height, weight, age, sex, date and time, and performs the operations necessary to measure the impedance, and extracts advisory data relevant to managing the patient's health. Outputs are provided to warning buzzer 29; output unit 30, which transmits to a printer of other peripheral device data such as measurement results. Battery 31 serves as the power supply for the device.

Electrode switch unit 32a and frequency switch unit 32b, supply inputs to signal generator 21 and differential amplifier 22 to switch selectively among electrodes 17, 18, 19 and 20 on grips 12 and 13 and among electrodes 55, 56, 57 and 58 on foot electrode unit 50. This input is connected by connector 66, cable 51 and connector 67. Switching is accomplished by making or breaking a circuit.

Electrode switch unit 32a and frequency switch unit 32b can include, for example, analog switches or relays. The type of switch used must conform to the setting of the measurement mode in CPU 28: A switch must be chosen which responds to the control signals for electrode and frequency switching carried out by the CPU.

Signals of frequency $f_1$ can travel from the subcutaneous fat layer both toward the external tissue (primarily the dermis) and toward the internal tissue (muscle, blood vessels, internal organs, bone, etc.). Signals of frequency $f_2$ travel from the subcutaneous fat layer primarily toward the internal tissue.

Figure 6:
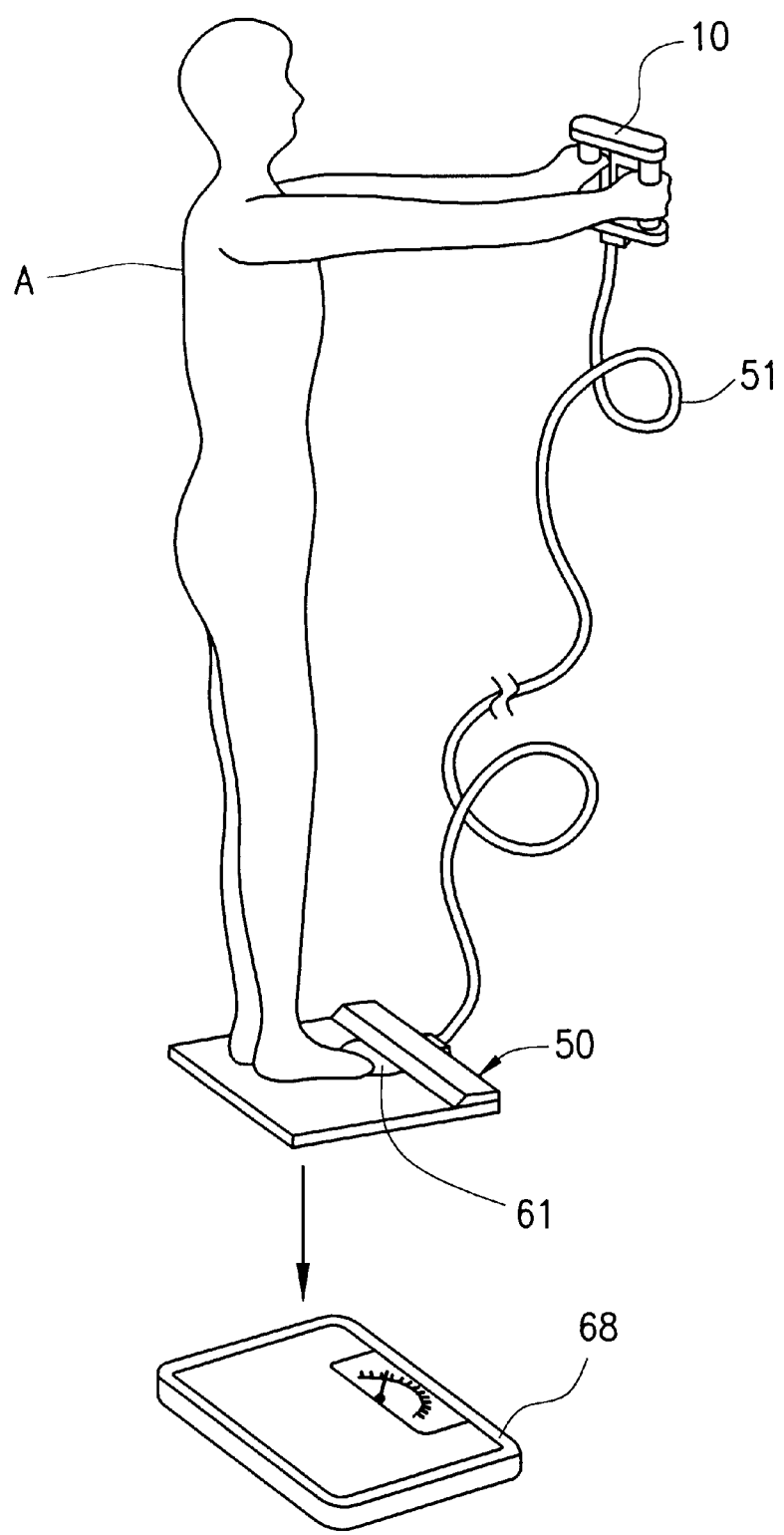
FIG. 6 illustrates another way the device of this same embodiment might be used.

The device described above allows data concerning physical characteristics to be input via input unit 15. The weight can be measured by an ordinary bathroom scale 68, on which foot electrode unit 50 can be placed, as shown in FIG. 6. In this case, the user steps onto foot unit 50, weighs himself on scale 68, and enters a current body weight. In this embodiment, foot electrode unit 50 has an opening 61 through which the user can read the weight from scale 68 while holding main unit 10, as shown in the drawing. A transparent window, which allows the weight to be read, may be substituted for this opening.

The proximity of the feet when the impedance between them was being measured could cause the thighs of some users to come in contact with each other. If this happened, the measurement path would vary and affect the accuracy of the measurements. In this embodiment, foot position guides 53 and 54 are provided on either side of opening 61 on foot electrode unit 50, and electrodes 55, 56, 57 and 58 are placed in these guides. The opening 61 has another, more indirect function, of ensuring a degree of separation between the feet.

The following explains the switching procedure which occurs in electrode switch unit 32a in the device described above when frequency $f_1$ is selected. First, to measure the impedance between the right hand and right foot, the mode for that measurement is set. A switching control signal from CPU 28 connects the switches of electrode switch unit 32a as shown in FIG. 4. Connection line $I_{h2}$ from electrode 18, the electrode which applies a high-frequency signal to the right hand, is connected to one terminal of signal generator 21a, and connection line $I_{f2}$ from electrode 55, the electrode which applies a high-frequency signal from the left foot, is connected to the other terminal. Connection line $E_{h2}$ from electrode 20, the electrode which measures the resistance of the right hand, and connection line $E_{f2}$ from electrode 58, the electrode which measures the resistance of the right foot, are connected to the two input terminals of differential amplifier 22. Connection line $I_{h1}$ from electrode 17, the electrode which applies a high-frequency signal to the left hand, and connection line $E_{h1}$ from electrode 19, the electrode which measures the resistance of the left hand, are not connected to anything —they are left open. Connection line $I_{f1}$ from electrode 55, the electrode which applies a high-frequency signal to the left foot, and connection line $E_{f1}$ from electrode 57, the electrode which measures the resistance of the right foot, are also not connected to anything and are left open.

Figure 7:
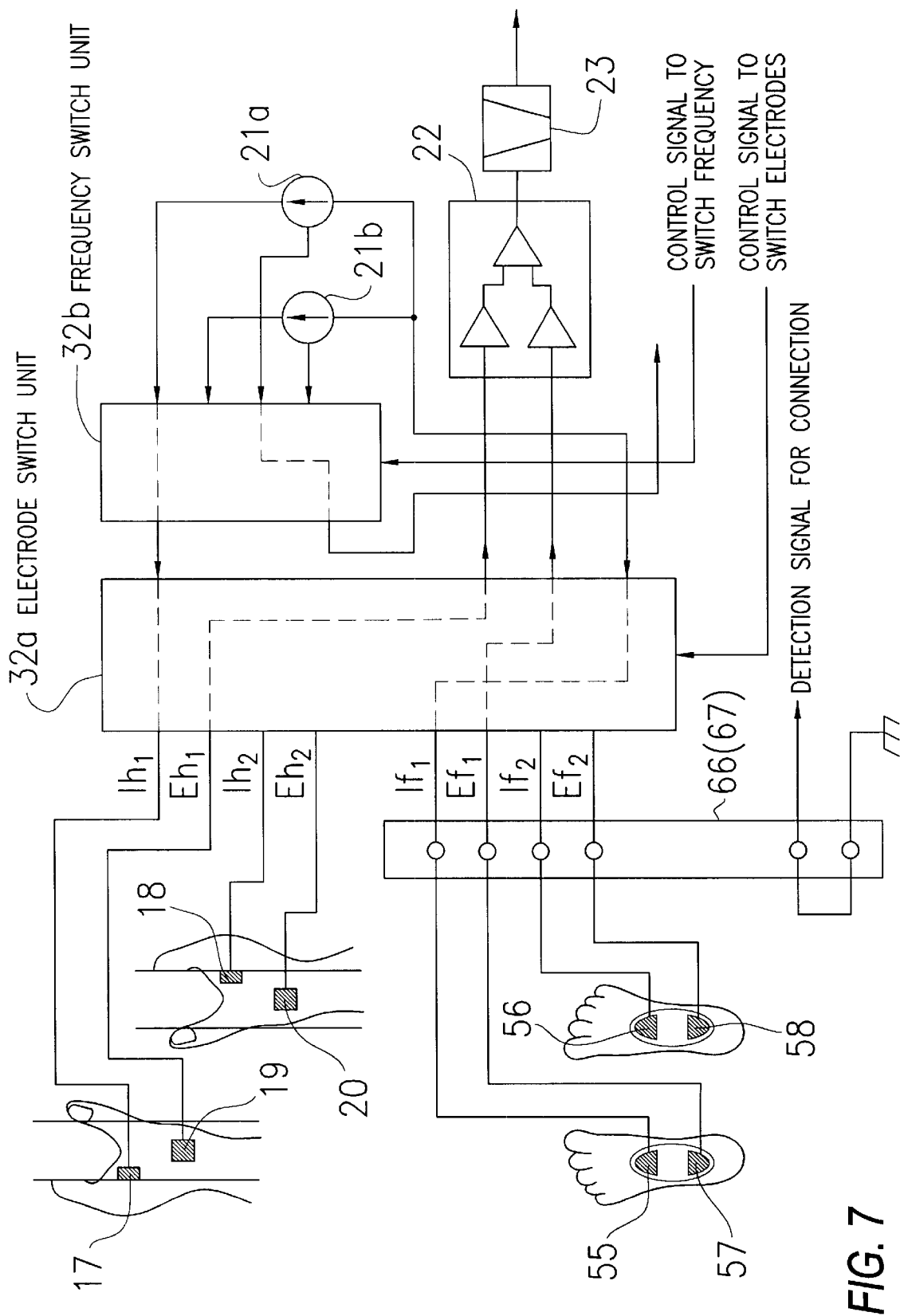
FIG. 7 is a circuit diagram illustrating the connections made when the device of the same embodiment is switched to the first frequency and set to the mode for measuring the impedance between left hand and foot.

When the mode is set to measure the impedance between the left hand and foot, a switching control signal from CPU 28 connects the switches in electrode switch unit 32a as shown in FIG. 7. A connection line $I_{h1}$ from electrode 17, the electrode which applies a high-frequency signal to the left hand, is connected to one terminal of signal generator 21a, and connection line $I_{f1}$ from electrode 55, the electrode which applies a high-frequency signal to the left foot, is connected to the other terminal. Connection line $E_{h1}$ from electrode 19, the electrode which measures the resistance of the left hand, and connection line $E_{f1}$ from electrode 57, the electrode which measures the resistance of the left foot, are connected to the two input terminals of differential amplifier 22. Connection line $I_{h2}$ from electrode 18, the electrode which applies a high-frequency signal to the right hand, and connection line $E_{h2}$ from electrode 20, the electrode which measures the resistance of the right hand, are not connected to anything and are left open. Connection line $I_{f2}$ from electrode 56, the electrode which applies a high-frequency signal to the right foot, and connection line $E_{f2}$ from electrode 58, the electrode which measures the resistance of the right foot, are also not connected to anything and are left open.

Figure 8:
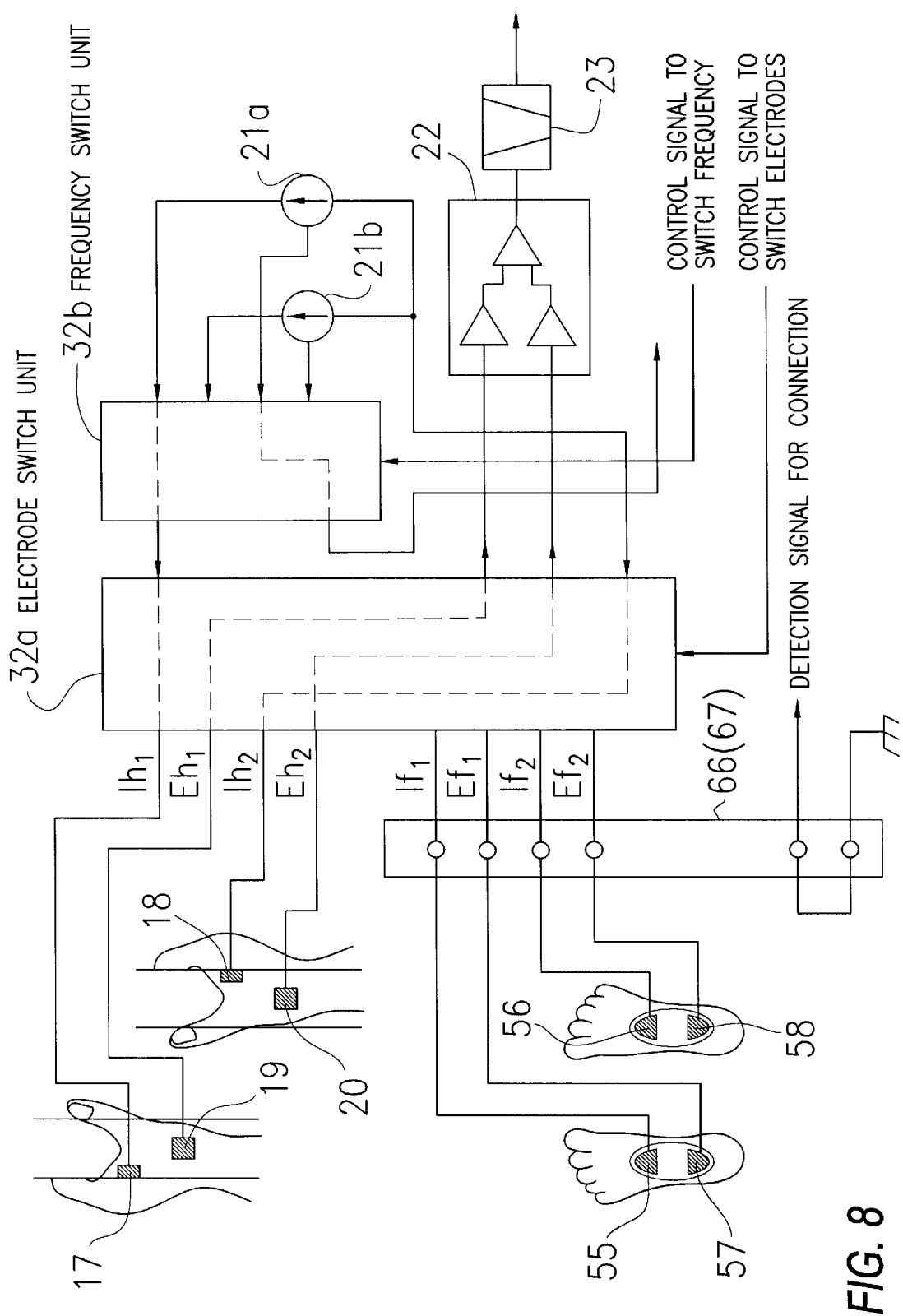
FIG. 8 is a circuit diagram illustrating the connections made when the device of the same embodiment is switched to the same frequency and set to the mode for measuring the impedance between the hands.

If the mode is set to measure the impedance between the hands, a switching control signal from CPU 28 causes the switches in electrode switch unit 32a to be connected as shown in FIG. 8. Connection line $I_{h1}$ from electrode 17, the electrode which applies a high-frequency signal to the left hand, is connected to one terminal of signal generator 21a, and connection line $I_{h2}$ from electrode 18, the electrode which applies a high-frequency signal to the right hand, is connected to the other terminal. Connection line $E_{h1}$ from electrode 19, the electrode which measures the resistance of the left hand, and connection line $E_{h2}$ from electrode 20, the electrode which measures the resistance of the right hand, are connected to the two input terminals of differential amplifier 22. In this case, as would be expected, connection lines $I_{f1}$, $I_{f2}$, $E_{f1}$ and $E_{f2}$, which are for the electrodes on the feet, are not connected and are left open.

Figure 9:
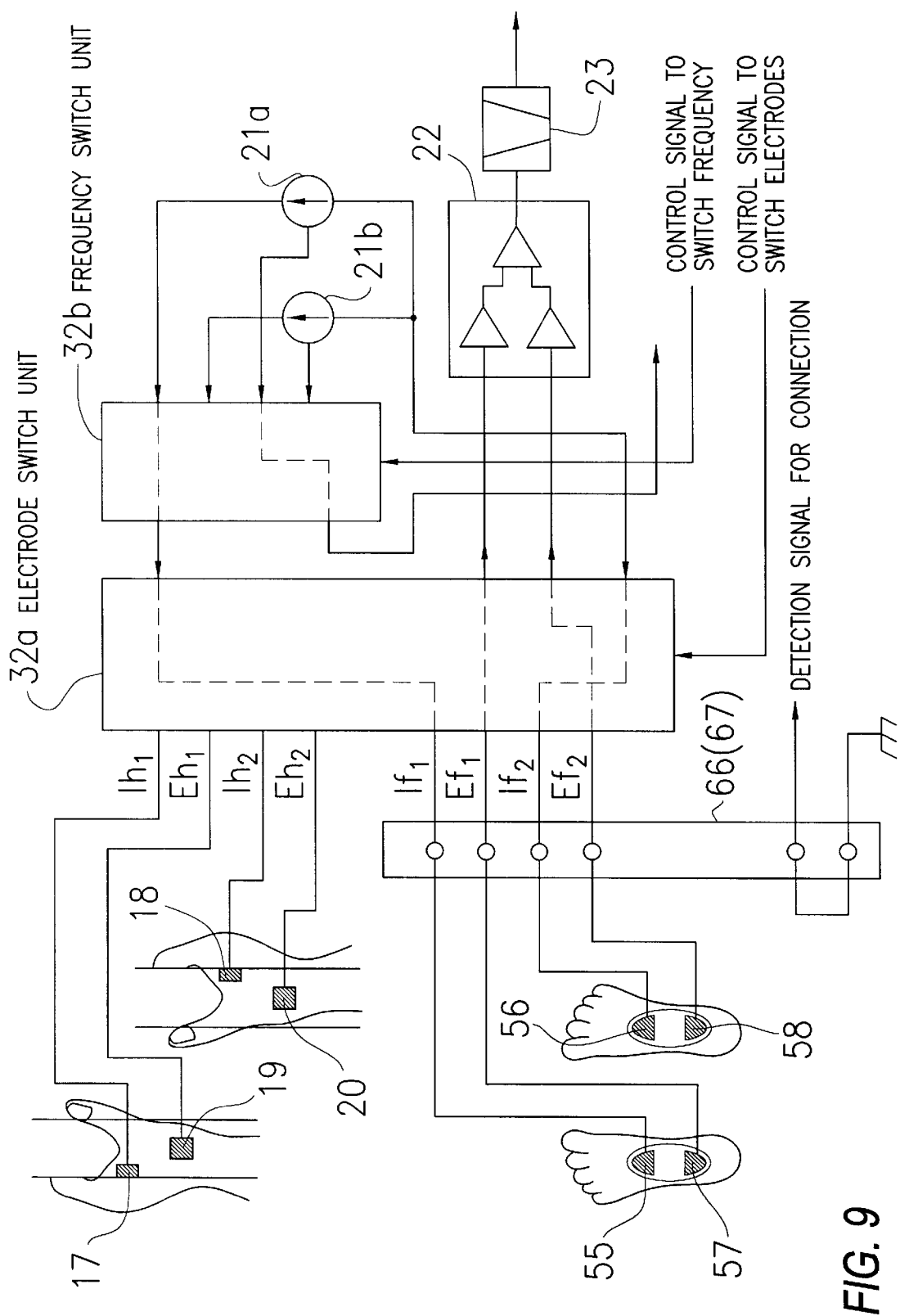
FIG. 9 is a circuit diagram illustrating the connections made when the device of the same embodiment is switched to the same frequency and set to the mode for measuring the impedance between the feet.

If the mode is set to measure the impedance between the feet, a switching control signal from CPU 28 causes the switches in electrode switch unit 32a to be connected as shown in FIG. 9. That is, connection line $I_{f1}$ from electrode 55, the electrode which applies a high-frequency signal to the left foot, is connected to one terminal of signal generator 21a, and connection line $I_{f2}$ from electrode 56, the electrode which applies a high-frequency signal to the right foot, is connected to the other terminal. Connection line $E_{f1}$ from electrode 57, the electrode which measures the resistance of the left foot, and connection line $E_{f2}$ from electrode 58, the electrode which measures the resistance of the right foot, are connected to the two input terminals of differential amplifier 22. In this case, the rule is reversed when measuring the impedance between the hands, and connection lines $I_{h1}$, $I_{h2}$, $E_{h1}$ and $E_2$, which are for the electrodes on the hands, are not connected and are left open.

Figure 10:
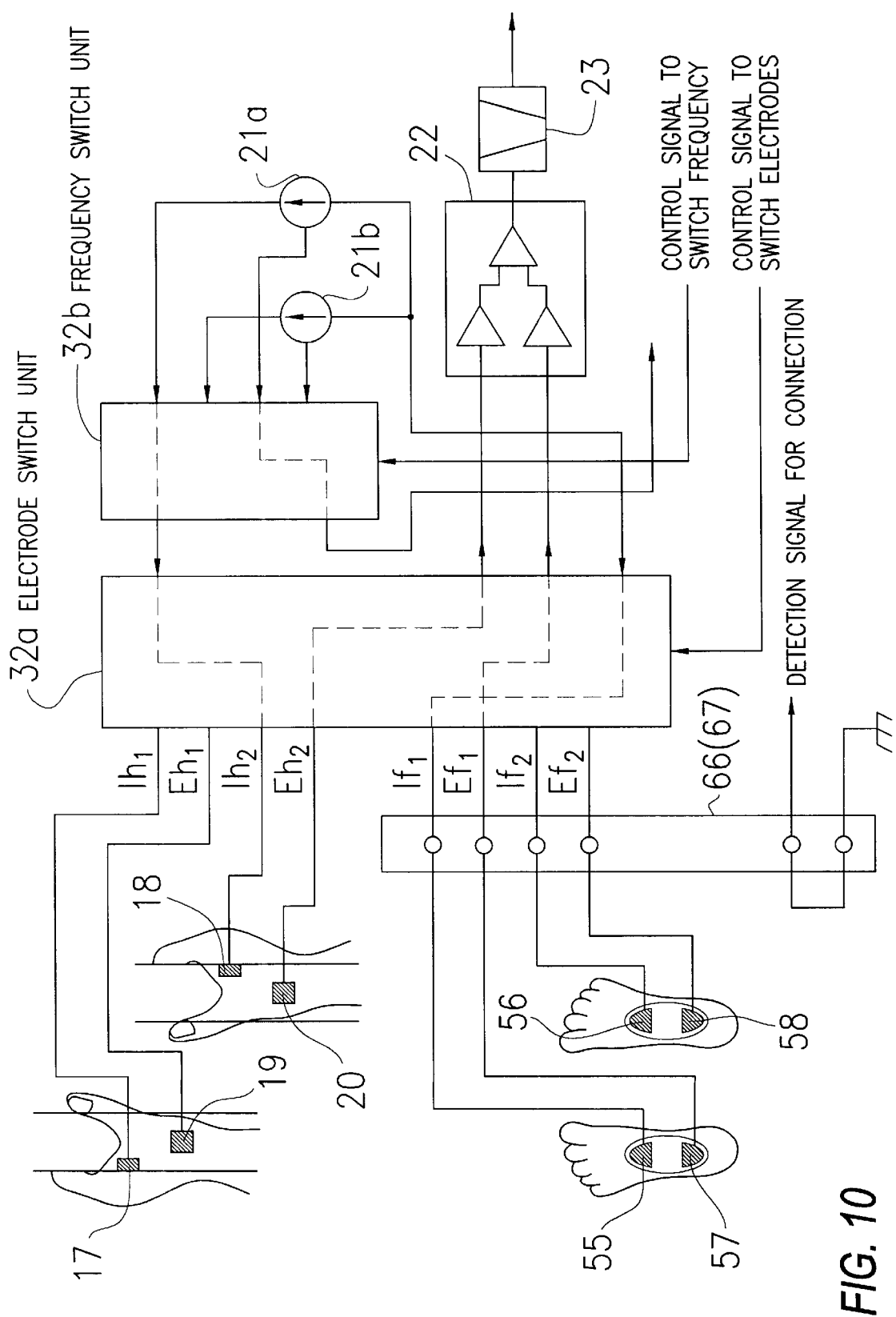
FIG. 10 is a circuit diagram illustrating the connections made when the device of the same embodiment is switched to the same frequency and set to the mode for measuring the impedance between the right hand and left foot.

By setting the mode to measure the impedance between the right hand and the left foot, a switching control signal from CPU 28 causes the switches in electrode switch unit 32a to be connected as shown in FIG. 10. That is, connection line $I_{h2}$ from electrode 18, the electrode which applies a high-frequency signal to the right hand, is connected to one terminal of signal generator 21a, and connection line $I_{f1}$ from electrode 55, the electrode which applies a high-frequency signal to the left foot, is connected to the other terminal. Connection line $E_{h2}$ from electrode 20, the electrode which measures the resistance of the right hand, and connection line $E_{f1}$ from electrode 57, the electrode which measures the resistance of the left foot, are connected to the two input terminals of differential amplifier 22. Connection line $I_{h1}$ from electrode 17, which applies a signal to the left hand, and connection line $E_{h1}$ from electrode 19, which measures the resistance of the left hand, are not connected anywhere, but are left open. Connection line $I_{f2}$ from electrode 56, which applies a signal to the right foot, and connection line $E_{f2}$ from electrode 58, which measures the resistance of the right foot, are also not connected anywhere, but are left open.

Figure 11:
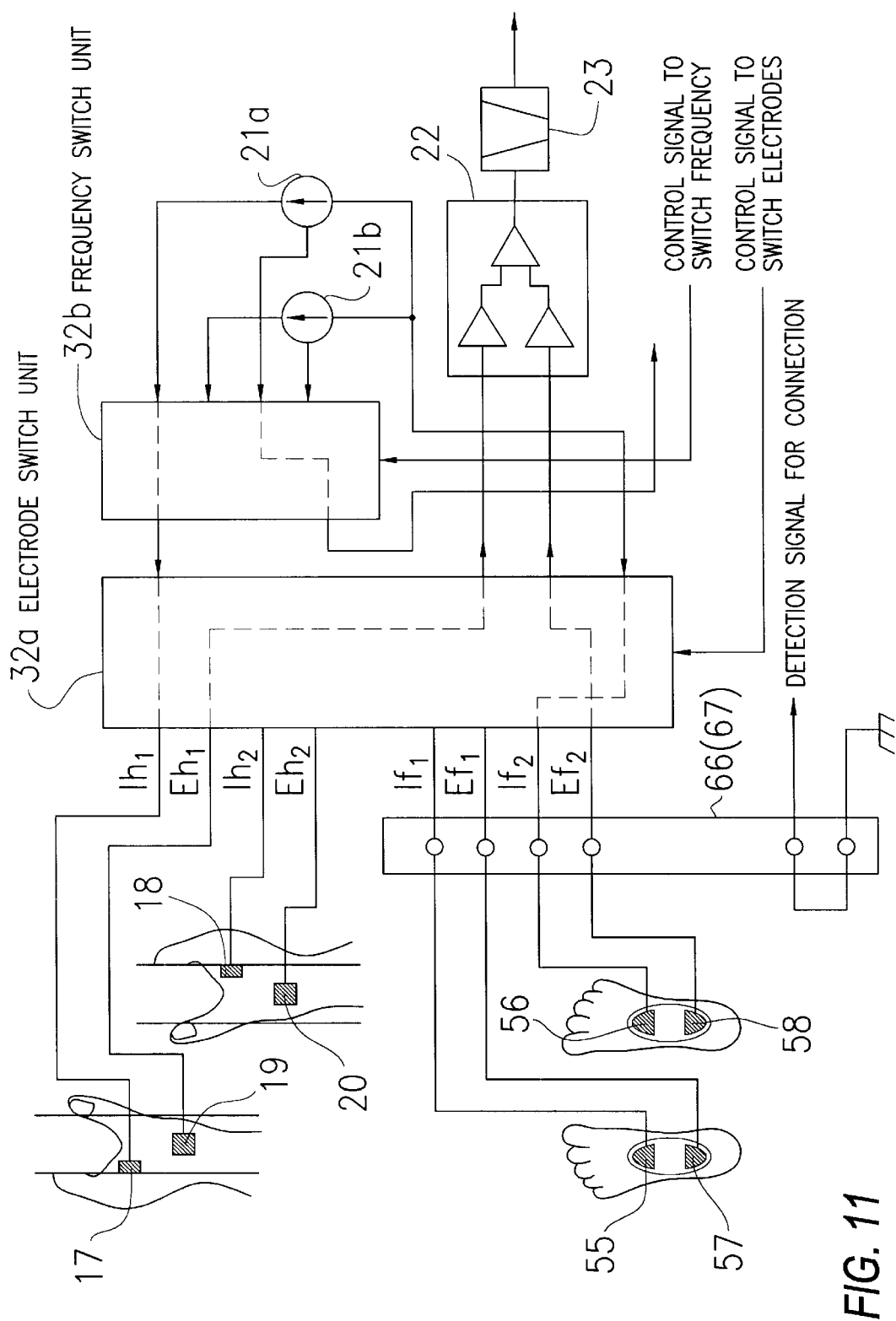
FIG. 11 is a circuit diagram illustrating the connections made when the device of the same embodiment is switched to the same frequency and set to the mode for measuring the impedance between the left hand and right foot.

When the mode is set to measure the impedance between the left hand and the right foot, a switching control signal from CPU 28 causes the switches in electrode switch unit 32a to be connected as shown in FIG. 11. This situation is just the opposite of that pictured in FIG. 10, with right and left hands and right and left feet exchanged. Since the connections are just the opposite of those shown in FIG. 10, further explanation is omitted.

Figure 12:
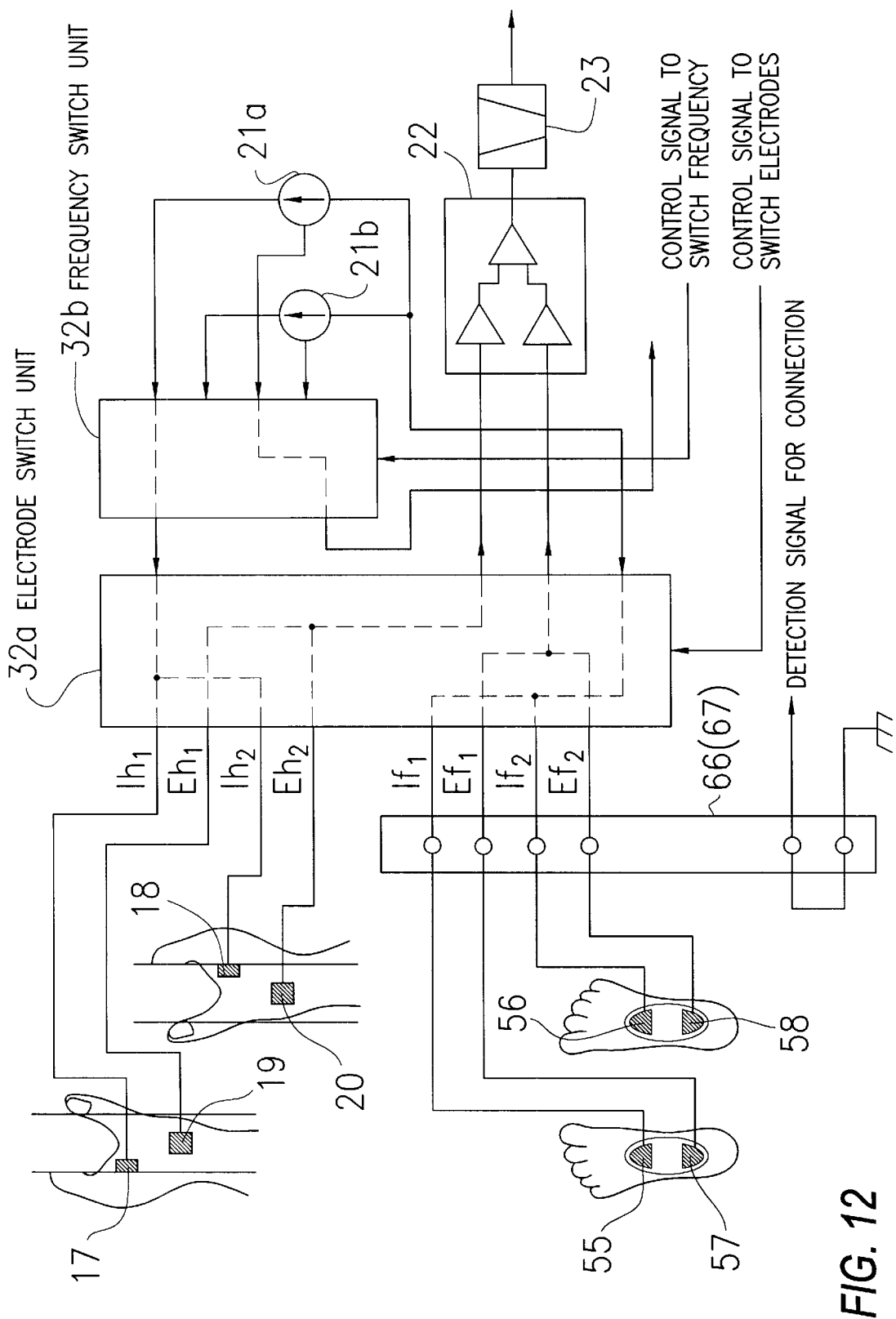
FIG. 12 is a circuit diagram illustrating the connections made when the device of the same embodiment is switched to the same frequency and set to the mode for measuring the impedance between both hands and feet.

To measure the impedance between both hands together and both feet together, CPU 28 provides a connection detection signal which is relayed to foot electrode unit 50 via cable 51, and applies a switching control signal which corresponds to the command for that mode. The circuits in electrode switch unit 32a are connected as shown in FIG. 12. Connection lines $I_{h1}$ and $I_{h2}$ from electrodes 17 and 18, the electrodes which apply a signal to the hands, are connected to one of the terminals on signal generator 21a. Connection lines $E_{h1}$ and $E_{h2}$ from electrodes 19 and 20, the electrodes which measure the resistance of the hands, are connected to one of the input terminals on differential amplifier 22. Connection lines $I_{f1}$ and $I_{f2}$ from electrodes 55 and 56, the electrodes which apply a signal to the feet, are connected in common to the other terminal on signal generator 21a.

Connection lines $E_{f1}$ and $E_{f2}$ from electrodes 57 and 58, the electrodes which measure the resistance of the feet, are connected in common to the other input terminal on differential amplifier 22.

To apply a signal of frequency $f_2$ and measure the impedance between the various parts of the body, frequency switch unit 32b in FIGS. 4 and 7 through 12 would be operated, and signal generator 21b would be connected instead of signal generator 21a.

The following description explains the principles by which body fat mass, visceral fat mass and other values can be calculated after measuring the impedance between various parts of the body using the device described above.

Calculation of Body Fat Mass (BFM)

Body fat mass is calculated using the results of impedance measurements made using a signal of the first frequency. This is the signal which will pass from the subcutaneous fat layer to both the external tissue (primarily the dermis) and the internal tissue (muscle, blood vessels, internal organs, bone, etc.).

(1) First calculate body density (BD).

$$BD = a - b \times W \times Z_1 / H^2$$

where a and b are constants determined by performing statistical processing on samples extracted randomly from the parent group of subjects, W is weight in kilograms, and H is height in centimeters.
Formula 1.

$Z_1(\Omega)$: measured impedance ($Z = \sqrt{R^2 + x^2}$)

(2) Next, determine ratio of body fat.

$$\% \text{Fat} = (4.95/BD - 4.5) \times 100$$

(3) From this ratio of body fat, BFM is calculated in kg.

$$BFM = W \times \frac{\% \text{ fat}}{100} \qquad \text{Formula 2.}$$

(4) The following calculation yields the lean body mass (LBM) or fat-free mass (FFM).

$$LBM = W \times (1 - \% \text{Fat}/100)$$

It is standard to measure the impedance $Z_1$ between the right hand and foot. However, in view of the disparities resulting from measuring the value from hand to hand or foot to foot, the inventors have decided that it may be best to use the average of the values obtained by measuring the impedance across all the limbs.

$$Z_{hf}^{bar} = (Z_{Rf-Rh} + Z_{Lh-Lf})/2 \text{ or}$$
$$= (Z_{Rh-Lf} + Z_{Lh-Rf})/2$$

Calculation of Visceral Fat Mass (VFM)

(1) The VFM is calculated based solely on the results of impedance measurements made using a signal of the second frequency. This is the frequency which passes from the subcutaneous fat layer primarily to the internal tissue.

$$VFM(kg) = aH_2/Z_{2S} + b/W + C$$

where a, b and c are constants determined by performing statistical processing on samples extracted randomly from the parent group of subjects; W is weight in kilograms; H is height in centimeters; and $Z_{2S}$ is the measured impedance (the impedance value when measured with a signal of the second frequency).

$$Z_{2S} = Z_{2b} - (Z_{2h} + Z_{2f})/2$$

$Z_{2b}$: Impedance between hand and foot
$Z_{2h}$: Impedance between the hands
$Z_{2f}$: Impedance between the feet
$Z_{2S}$: Impedance of the thoracic region The standard measurement of $Z_{2b}$ is made between right hand and foot. However, in view of the disparities of balance resulting from measuring the value from hand to hand or foot to foot, the inventors decided that it would be best to use the average of the values obtained by measuring the impedance across all the limbs.

(2) The VFM is calculated based on the results when the impedance is measured using signals of both the first and second frequency. (The standard measurement is made from one hand to one foot.)

$$BFM = \frac{1}{a \times \frac{1}{W} - b \times Z_1/H^2} - C \times W \qquad \text{Formula 3.}$$

0035.

$$VFM = \frac{1}{a' \times \frac{1}{W} - b \times Z_1\left(\alpha \frac{Z_{2S}}{Z_{1S}} + \beta\right) / H^2 + d} - C' \times W \qquad \text{Formula 4.}$$

Here a, b, c, d, a', b', C', $\alpha$ and $\beta$ are constants determined by performing statistical processing on samples extracted randomly from the parent group of subjects; $Z_1$ ($\Omega$) is the value of the impedance measured between one hand and foot using a signal of the first frequency; $Z_{1S}$ ($\Omega$) is the value of the impedance of the thoracic region measured using a signal of the first frequency; $Z_{1S} = A_1 - (Z_{1h} + Z_{1f})/2$; $Z_{1h}$ is the impedance between the hands; $Z_{1f}$ is the impedance between the feet; and $Z_{2S}$ ($\Omega$) is the value of the impedance of the thoracic region measured using a signal of the second frequency. Visceral Fat Mass (VFM), Body Fat Ratio (% Fat) and Visceral-to-Subcutaneous Ratio (V/S Ratio) are determined by the following calculations.

$$SFM = BFM - VFM$$

$$\% \text{Fat} = BFM/W \times 100$$

$$V/S = VFM/SFM$$

A V/S ratio greater then 0.5 indicates visceral-type obesity; a V/S ratio less than 0.5 indicates the subcutaneous-type.

(3) VFM is calculated based on the results of measuring the impedance using signals of both the first and second frequency. (The standard measurement is made between both hands and both feet.)

The estimation scheme is identical to that used above in (1) and (2); however, the method of calculating $Z_1$, $Z_{1S}$ and $Z_{2S}$ differs as follows.

Calculation of $Z_1$ $$Z_1 = Z_{1W} + (Z_{1h} + Z_{1f})/4$$

$Z_{1W}$: Impedance between both hands and both feet (measured using a signal of the first frequency)
$Z_{1h}$: Impedance between the hands (measured using a signal of the first frequency)

$Z_{1f}$: Impedance between the feet (measured using a signal of the first frequency)

Calculation of $Z_{1S}$ $$Z_{1S}=Z_{1W}-(Z_{1h}+Z_{1f})/4$$

Calculation of $Z_{2S}$ $$Z_{2S}=Z_{2W}-(Z_{2h}+Z_{2f})/4$$

$Z_{2W}$: Impedance between both hands and both feet (measured using a signal of the second frequency)
$Z_{2h}$: Impedance between the hands (measured using a signal of the second frequency)
$Z_{2f}$: Impedance between the feet (measured using a signal of the second frequency)

The operation of this system will now be described with reference to the flowcharts in FIGS. 13, 14 and 15. The impedance as measured between one hand and one foot shall be used as a standard.

When power supply switch 14 is turned on, various preparatory procedures are performed. The RAM is initialized, the circuit elements and display elements are checked, and so on (Step, hereafter ST 1). The user enters, via input unit 15, his or her characteristic physical data, including height, weight, age, sex, and waist-to-hip ratio, as well as the data and time (ST 2). Until all the data have been input, the device stands by (ST 2 and ST 3). When data entry is completed, the CPU determines whether the foot electrode unit is connected (ST 4) by determining whether there is a connection detection signal from connector 66 or 67 in the circuit shown in FIGS. 4 and 5.

If the determination in ST 4 was "no", a message will be displayed on display 16 to the effect that the foot electrodes must be connected, to inform the user (ST 5). If the determination in ST 4 was "yes", frequency $f_1$ is selected, voltage switch unit 32b and signal generator 21a are chosen, and the voltage selection flag is set (ST 6). Electrode switch unit 32a is set to the mode for measuring impedance between the right hand and foot, and the identification code is set to select right hand and right foot (ST 7).

When the setting of the switches is completed, the device stands by until the start switch on input unit 15 is actuated (ST 8). After the switches have been set, a command such as "Actuate start switch" can appear on display 16 to encourage the user to operate the key. When the start switch is turned on, there is a time delay of several seconds (ST 9), after which buzzer 29 or display 16 is used to inform the user that measurement has begun (ST 10). The time delay in ST 9 after the start switch is turned on should be sufficient to allow the user to grasp grips 12 and 13 completely and correctly and to ensure proper foot placement into position guides 53 and 54.

When impedance is measured, a check is made as to whether the value obtained is stable and in the correct range (ST 11 and 12). If the value is not stable, a message such as "Hands and feet must make good contact with the electrodes" can be shown on display 16 and buzzer 29 can warn the user (ST 13). If the value measured is found to be correct and stable in ST 12, the measurement operation is executed (ST 14), and a determination is made as to whether the signal being applied has the first frequency (ST 15). Since at this time the determination will be "yes", flow proceeds to a determination as to whether the selection code for the electrode switch unit has been set to "right hand, right foot" (ST 16). Since this determination will also be "yes" at this time, the measurement result, i.e., the impedance value which was measured, will be stored in the memory area as right hand-right foot impedance $Z_{Rh-Rf}$ (ST 17). Electrode switch unit 32a will be switched to left hand-left foot mode, and the identification code will be changed to select left hand-left foot (ST 18). Program flow now returns to ST 11, and the impedance $Z_{Lh-Lf}$ between the left hand and foot is measured in ST 11 through 14. The determination in ST 15 of whether the signal applied was of the first frequency will again be "yes", just as it was the first time through; however, the determination in ST 16, whether the identification code for the electrode switch unit has been set to right hand-right foot, will now be "no", since the code was changed to left hand-left foot in ST 18. Flow then proceeds to ST 19.

In ST 19, the right hand-right foot impedance value $Z_{Rh-Rf}$ is read out of the memory area where it was stored and added to the left hand-left foot impedance value $Z_{Lh-Lf}$ to calculate the average value $Z_1$, which is equal to $(Z_{Rh-Rf}+Z_{Lh-Lf})/2$ (ST 20). The average value $Z_1$ is stored in the memory area (ST 21), frequency switch unit 12b is switched to the second measurement frequency, and the frequency selection flag is reset (ST 22). The resetting of this flag indicates that the second frequency, frequency $f_2$, has now been selected.

Once the frequency selection flag has been reset in ST 22, flow returns to ST 11, and impedance $Z_{Lh-Lf}$ is measured between the left hand and left foot in ST 11 through 14. The determination in ST 15, whether the signal applied was of the first frequency, will be "no", so program flow passes to ST 23, which queries whether the identification code for the electrode switch unit is set to left hand-left foot. The answer here is "yes", so the impedance value $Z_{Lh-Lf}$ which was measured is stored at this time in the memory area (ST 24). Flow now reverts to the right hand-right foot measurements mode, changes the identification code back to the code to select right hand-right foot (ST 25), and returns to ST 11.

In ST 11 through 14, the impedance $Z_{Rh-Rf}$ between right hand and right foot is measured by applying a signal of frequency $f_2$. The determination in ST 15 and 23 will be "no", so flow proceeds to ST 26, which queries whether the code is that for right hand-right foot. When the result is "yes", the impedance value $Z_{Lh-Lf}$ which was previously stored in the memory area (ST 27) is read out. The right hand-right foot vale $Z_{Rh-Rf}$ and the left hand-left foot value $Z_{Lh-Lf}$ are used to calculate the average value $Z_{2b}$ using $Z_{2b}=(Z_{Rh-Rf}+Z_{Lh-Lf})/2$ (ST 28). This average value $Z_{2b}$ is stored in the memory area (ST 29), electrode switch unit 32a is switched to the hand-to-hand mode, the identification code is changed to select hand-to-hand (ST 30), and returns to ST 11.

ST 11 through 14 measure the impedance $Z_{2h}$ between the hands. Since the determinations in ST 15, 23 and 26 are all "no", flow proceeds to ST 31, where the process determines if the identification code selects hand-to-hand. The answer is "yes", so the hand-to-hand impedance value $Z_{2h}$ which was measured is stored in the memory area (ST 32). Electrode switch unit 32a is switched to foot-to-foot measurement mode, the identification code is changed to select foot-to-foot (ST 33), and flow returns to ST 11.

ST 11 through 14 measure the impedance $Z_{2f}$ between the feet. Since the determinations in ST 15, 23, 26 and 31 are all "no", flow proceeds to ST 34, where the average hand-foot impedance value $Z_{2b}$ and the hand-to-hand impedance value $Z_{2h}$ are read from the memory. From impedance values $Z_{2b}$ and $Z_{2h}$ and the foot-to-foot impedance value $Z_{2f}$, the impedance $Z_{2S}$ of the thoracic region is calculated using $Z_{2S}=Z_{2b}-(Z_{2h}+Z_{2f})/2$ (ST 25). The personal data, including weight, height, and so on, are read out of the memory area (ST 36). The personal data and the calculated value $Z_{2S}$ are substituted in the formula to estimate VFM, and the VFM is calculated (ST 37).

The average value $Z_1$ for hand-foot impedance as measured with a signal of the first frequency is read out of the memory area (ST 38). The personal data and value $Z_1$ are substituted in the formula to estimate body fat ratio, and the body fat ratio is calculated (ST 39). Body fat mass is calculated using the formula BFM–W×% Fat/100 (where W is weight) (ST 40). Subcutaneous fat mass is calculated using the formula SFM=BFM–VFM, and the visceral-to-subcutaneous ratio is obtained by V/S=VFM/SFM (ST 41).

A determination is made as to whether the V/S ratio is less than 0.5 (ST 42) If V/S is less than 0.5, a determination is made that the obesity is of the subcutaneous type (ST 42). If the ratio exceeds 0.5, the obesity is judged to be of the visceral type (ST 43). The fact that all measurements and calculations have been completed is conveyed by display 16 and buzzer 29 (ST 45). The results of the calculations and advisory data are displayed on display 16 or output to the exterior via a communication device (ST 46).

Figure 16:
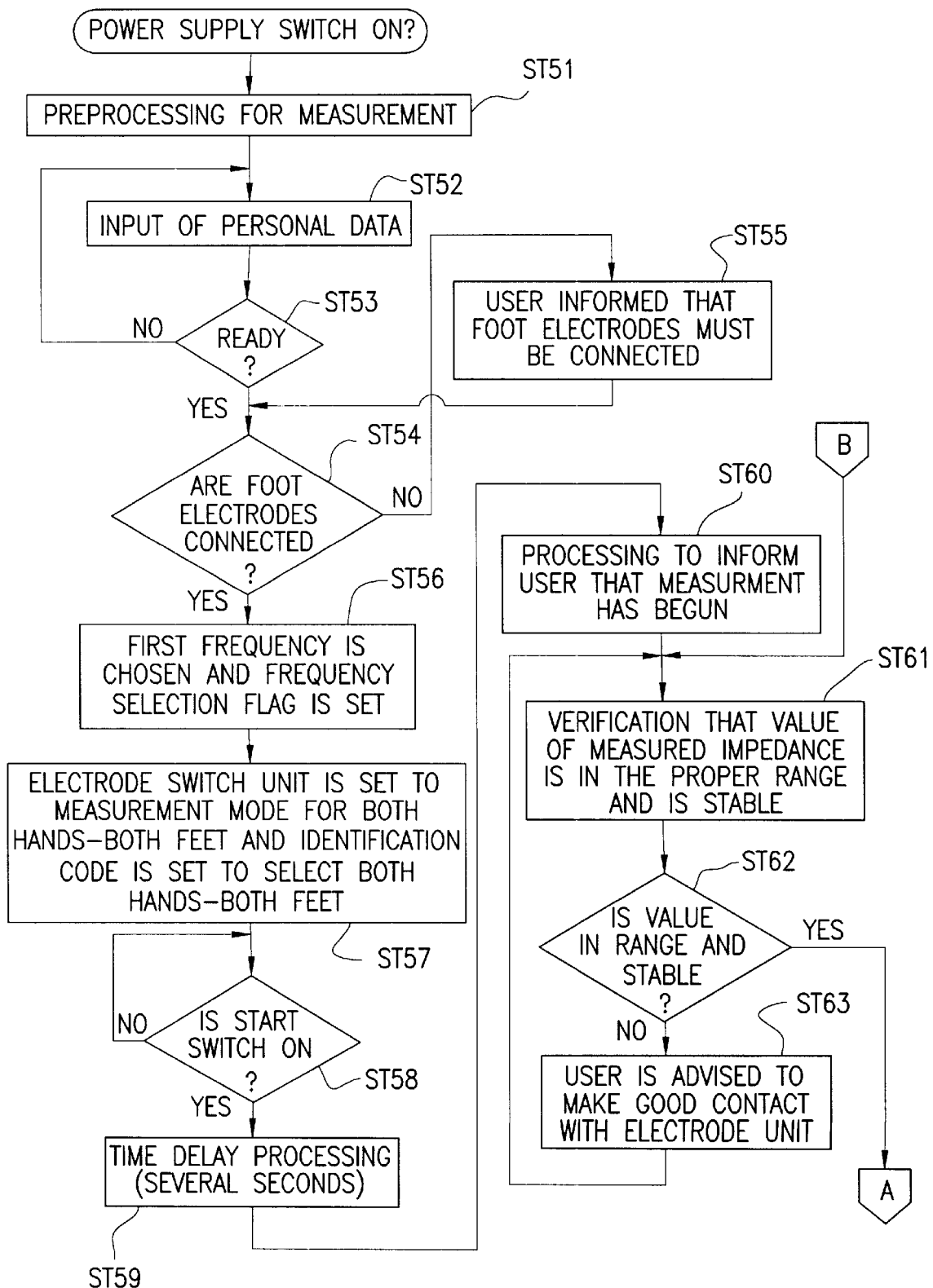
FIG. 16 is a flowchart of the operations performed when the same embodiment uses as its standard mode the measurement of the impedance between both hands and feet.
Figure 17:
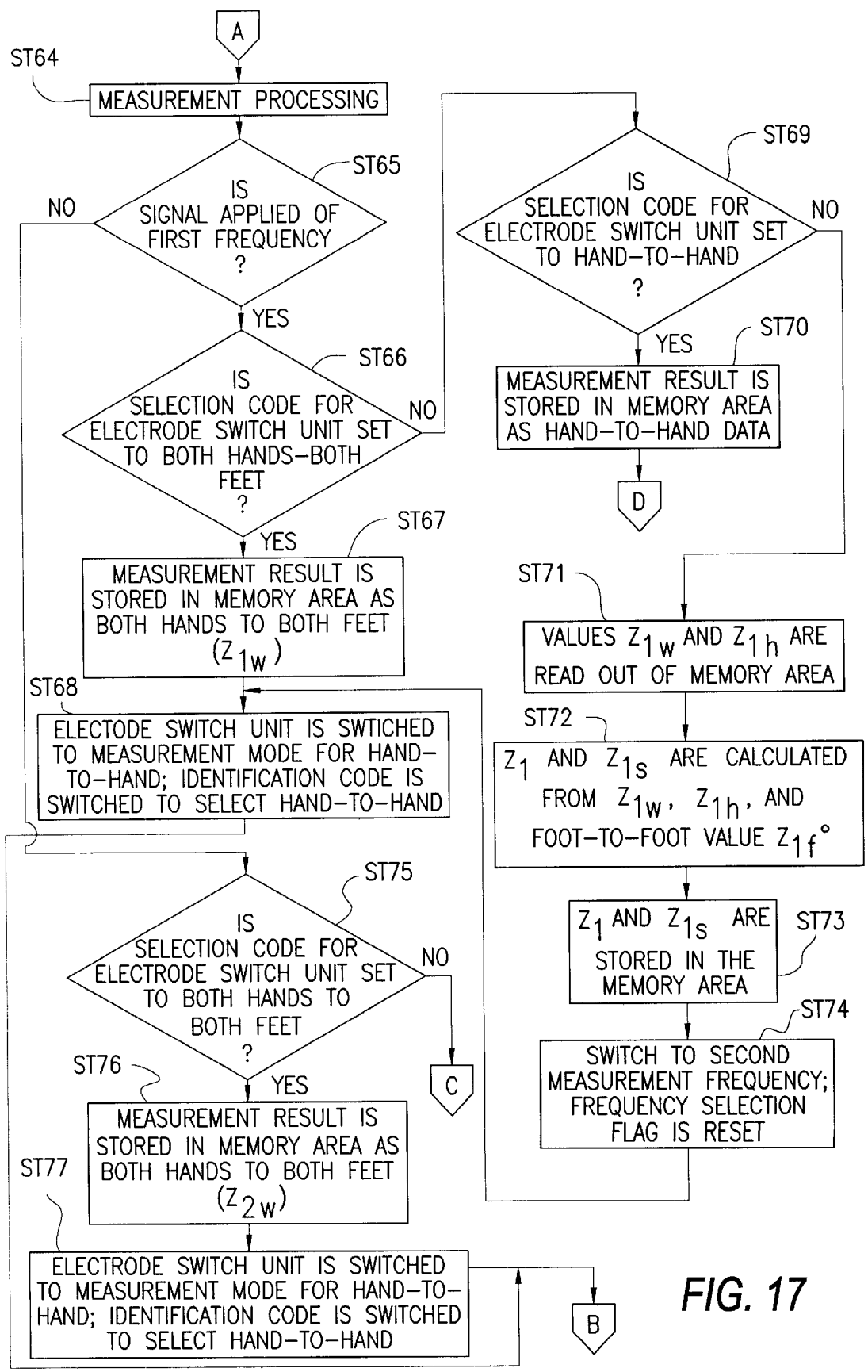
FIG. 17 is another flowchart of the measurement operations performed by the same embodiment.
Figure 18:
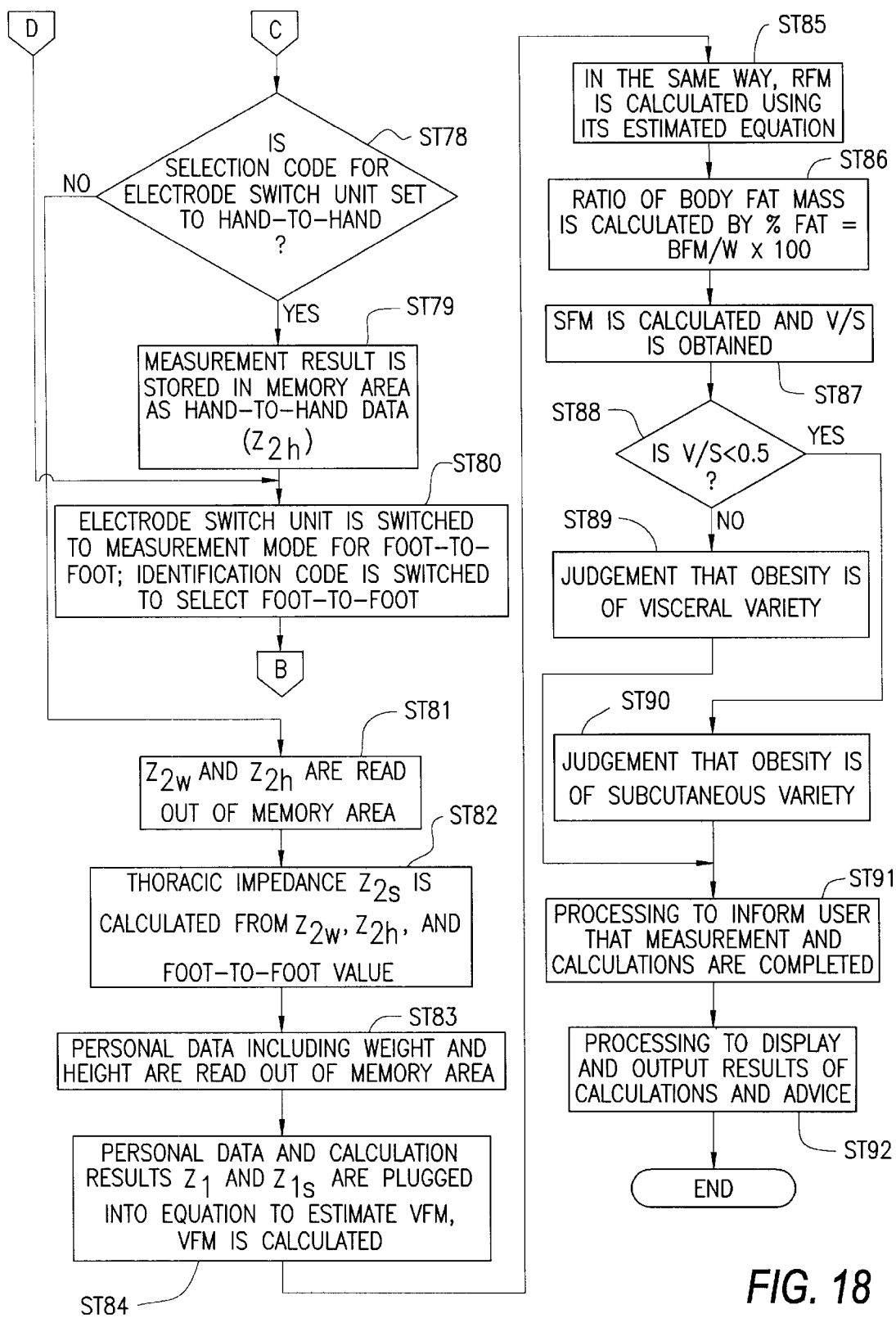
FIG. 18 is another flowchart of the measurement operations performed by the same embodiment.

The following explains the operation of an embodiment in which the standard measurement mode is between both hands and feet, with reference to the flowcharts shown in FIGS. 16, 17 and 18.

The initial processing performed when power supply switch 14 is actuated include ST 51 through 56, and are identical to ST 1 through 6 of measuring the impedance across one hand and foot. In ST 57 electrode switch unit 32*a* is set to measurement mode for both hands-both feet, and the identification code is set to both hands-both feet. When the setting of the switches has been completed, the device stands by until the start switch on input unit 15 is actuated (ST 58). When the start switch is turned on, there is a time delay identical to that experienced when measuring impedance between one hand and foot (ST 59). The user is informed that measurement has begun (ST 60), and the impedance $Z_{1W}$ between both hands and both feet is measured through the processing performed in ST 61 through 64.

A determination is made as to whether the signal applied was of the first frequency (ST 65). Since initially this determination will be "yes", flow proceeds to the determination of whether the selection code for the electrode switch unit is set for both hands-both feet (ST 66). This determination is also "yes" at this time, so the impedance $Z_{1W}$ between both hands and feet is stored in the memory area (ST 67). Electrode switch unit 32*a* is switched to hand-to-hand mode, and the identification code is changed to that which selects hand-to-hand (ST 68). Flow returns to ST 11, where the impedance $Z_{1h}$ between the hands is measured in ST 61 through 64. The determination in ST 65, whether the signal applied is of the first frequency, is still "yes", but the determination is ST 66, whether the identification code for the electrode switch unit is set to select both hands-both feet, is now "no", since the code was changed to select hand-to-hand in ST 68, so flow proceeds to ST 69. The determination in ST 69, whether the selection code is set to hand-to-hand, is "yes", so the measurement result $Z_{1W}$ is stored in the memory area (ST 70). The electrode switch unit is changed to foot-to-foot mode (ST 80), the identification code is changed to select foot-to-foot, and flow returns to ST 61.

In ST 61 through 64, the impedance $Z_f$ between the feet is measured. The determinations in ST 65, 66 and 69 are all "no", so flow proceeds to ST 71. In this step, impedance $Z_{1W}$, measured between both hands and feet, and impedance $Z_{1h}$, measured between the hands, are read out of the memory area where they have been stored. Using $Z_{1W}$, $Z_{1h}$, and impedance $Z_{1f}$, measured between the feet, $Z_1$ is obtained by solving $Z=Z_{1W}+(Z_{1h}+Z_{1f})/4$, and $Z_{1S}$ is obtained by solving $Z_{1S}=Z_{1W}-(Z_{1h}+Z_{1f})/4$ (ST 72). $Z_1$ and $Z_{1S}$ are stored in the memory area (ST 73), the frequency switch unit is switched to select the second measurement frequency, frequency $f_2$, and the frequency selection flag is reset (ST 74). The electrode switch unit is changed to hand-to-hand measurement mode, the identification code is changed to select hand-to-hand measurement mode (ST 68), and flow returns to ST 61.

In ST 61 through 64, the impedance $Z_{2h}$ between the hands is measured using a signal of frequency $f_2$. The determinations in ST 65 and 75 are both "no", so flow proceeds to ST 78, which required a determination as to whether the code is set to select hand-to-hand impedance. The answer is "yes", so the measurement result, i.e., impedance $Z_{2h}$ measured between the hands, is stored in the memory area (ST 79). The electrode switch unit is changed to foot-to-foot measurement mode, the identification code is changed to select foot-to-foot (ST 80), and flow returns to ST 61.

In ST 61 through 64, the impedance $Z_{2f}$ between the feet is measured. The determination in ST 65, 75 and 78 are all "no", so flow proceeds to ST 81 where impedance $Z_{2W}$ measured between both hands and feet, and impedance $Z_{2h}$ measured between the hands, are read out of the memory area where they have been stored. Using $Z_{2W}$, $Z_{2h}$, and impedance $Z_{2f}$, measured between the feet, the impedance $Z_{2S}$ of the thoracic region can be calculated by solving $Z_{2S}=Z_{2W}-(Z_{2h}+Z_{2f})/4$ (ST 82). The personal data, including weight, height, and so on, are read out of the memory area (ST 83). The personal data and the calculated value $Z_{2S}$ are substituted in the formula to estimate VFM, and the VFM is calculated (ST 84). In the same way, BFM is calculated using the BFM estimation scheme (ST 85). Weight W is read out, and the body fat ratio is calculated by solving % Fat=(BFM/W)×100 (ST 86). The subcutaneous fat mass is calculated by SFM=BFM–VFM, and the visceral-to-subcutaneous ratio is obtained by V/S=VFM/SFM (ST 87).

Just as in ST 42 through 46 when measuring one hand and foot, a determination is made as to whether V/S is less than 0.5 (ST 88). If it is, the obesity is judged to be of the subcutaneous type (ST 90). If V/S exceeds 0.5, it is judged to be of the visceral type (ST 89). The fact that all measurements and calculations have been completed is conveyed by display 16 and buzzer 29 (ST 91). The results of the calculations and advisory data are displayed on display 16 or output via a communication device (ST 92).

It is well known that the ratio of body fat and body fat mass calculated using the impedance measured between parts of the body with standard voltage measurements, as described above, and the W/H (waist-to-hip) ratio can be used to estimate the ratio of visceral-to-subcutaneous, fat mass, the visceral fat mass, and other useful values. This is discussed in further detail herein.

Figure 19:
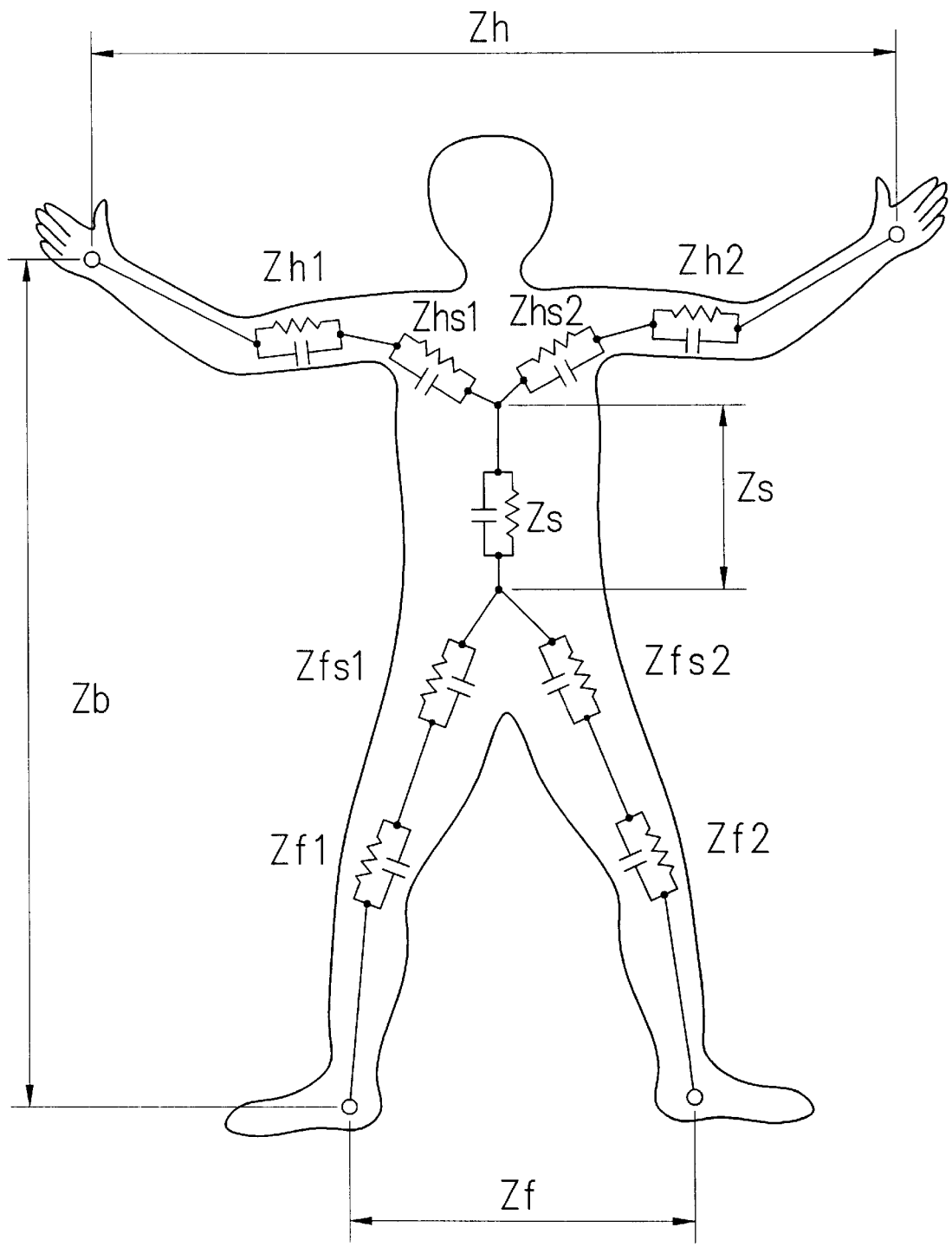
FIG. 19 shows the equivalent circuits of the human body which are relevant to measuring the impedance values used to estimate the waist/hip ratio.

The impedance across the various parts of the human body is represented in an equivalent fashion in FIG. 19. The impedance $Z_{fS}$ (=$Z_{fS1}$, =$Z_{fS2}$), which is found within the impedance $Z_f$ measured between the feet, contains data concerning the hips (H). The impedance $Z_S$ measured in the center of the thoracic region contains data concerning the waist.

The arms and legs generally develop in balance with each other. Both the arms and legs of a large-boned person will be thick. Similarly, a muscular person will generally have arms and legs which are equally developed. This makes it possible to extract $Z_{fS}$ by subtracting $Z_h$ from $Z_f$ and dividing. It follows, then, that $W/H = Z_S/Z_{fS}$ $Z_S = Z_b - (Z_h + Z_f)/2$ $Z_{fS} = \alpha_1 Z_f - \beta_1 Z_h + \gamma_1$, and $Z_h > Z_{hS1} = Z_{hS2}$ $\alpha_1$, $\beta_1$ and $\gamma_1$ are constants
From the above, W/H is calculated.

$$W/H = Z_s \cdot \frac{Z_h}{\alpha_2 Z_f + \beta_2} \cdot f \quad \text{(Height and weight data)} \qquad \text{Formula 5.}$$

Here f (height and weight data) is revised to correspond to personal data concerning height and weight, and $\alpha_2$ and $\beta_2$ are constants.

Figure 20:
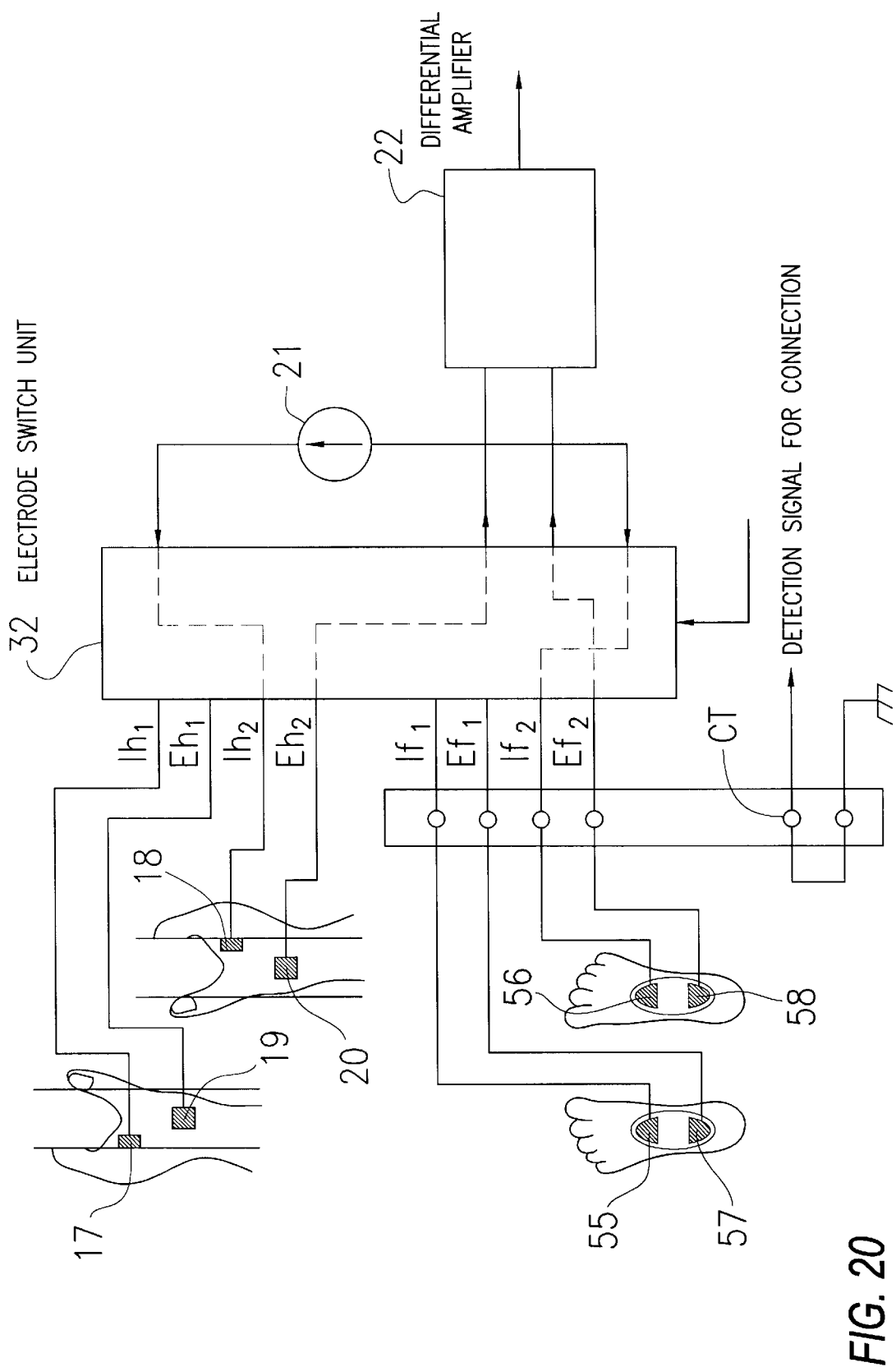
FIG. 20 is a block diagram illustrating the circuits in another ideal embodiment of the device to provide data as a guide to health management of this invention.

A partial circuit diagram for the device of this embodiment, which estimates the W/H ratio using the impedance values measured and uses the various impedance values and the W/H ratio to estimate VFM, the visceral-to-subcutaneous fat ratio and other values, is shown in FIG. 20. Unlike the device pictured in FIGS. 4 and 5, the device of this embodiment has only one frequency switch unit, 32, which corresponds to unit 32a in the earlier embodiment. The rest of this device, including the circuitry beyond differential amplifier 22, which is not shown, is identical to the previous embodiment, and hence a detailed explanation is omitted.

Figure 21:
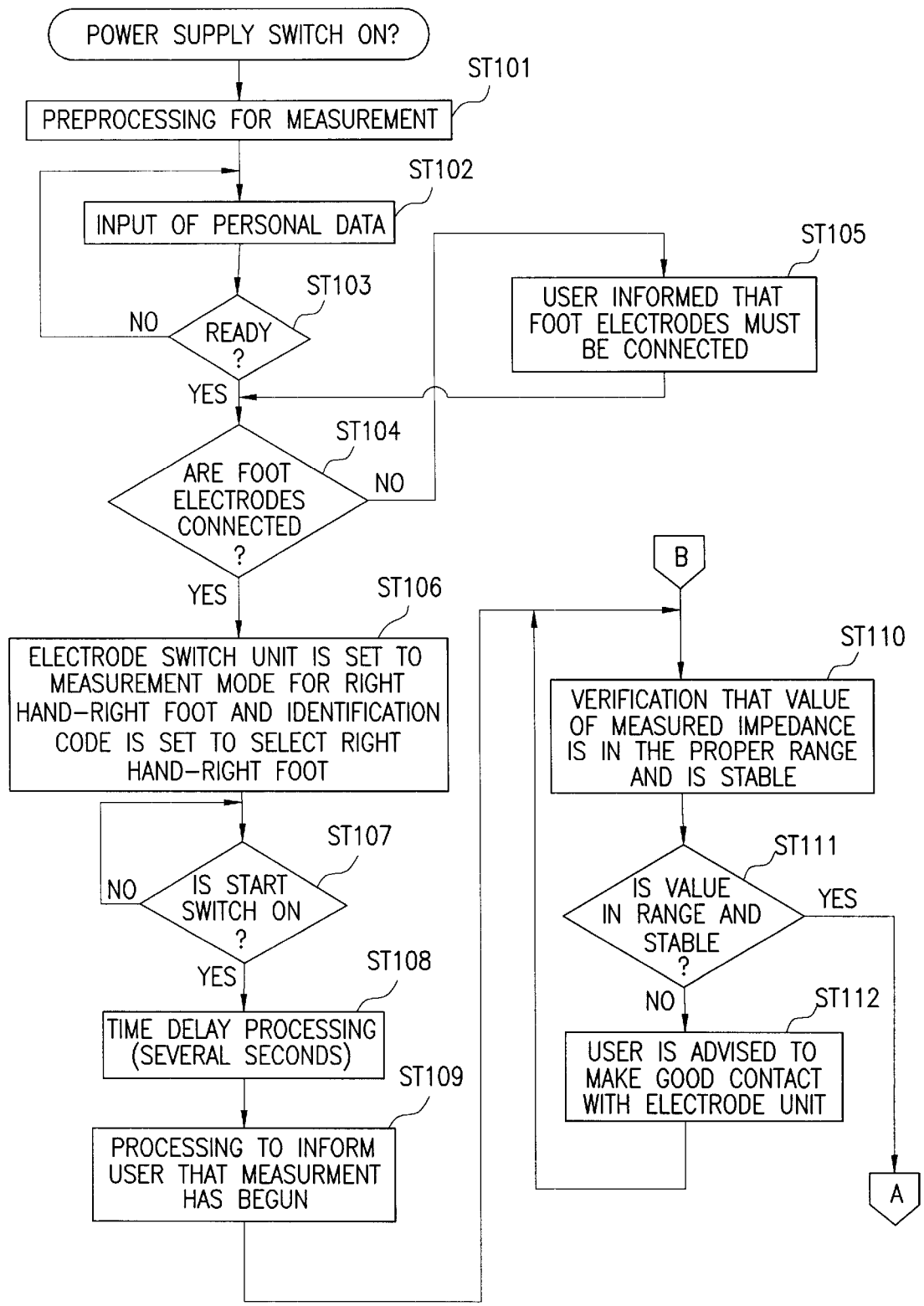
FIG. 21 is a flowchart of the measurement operations performed by this device.
Figure 22:
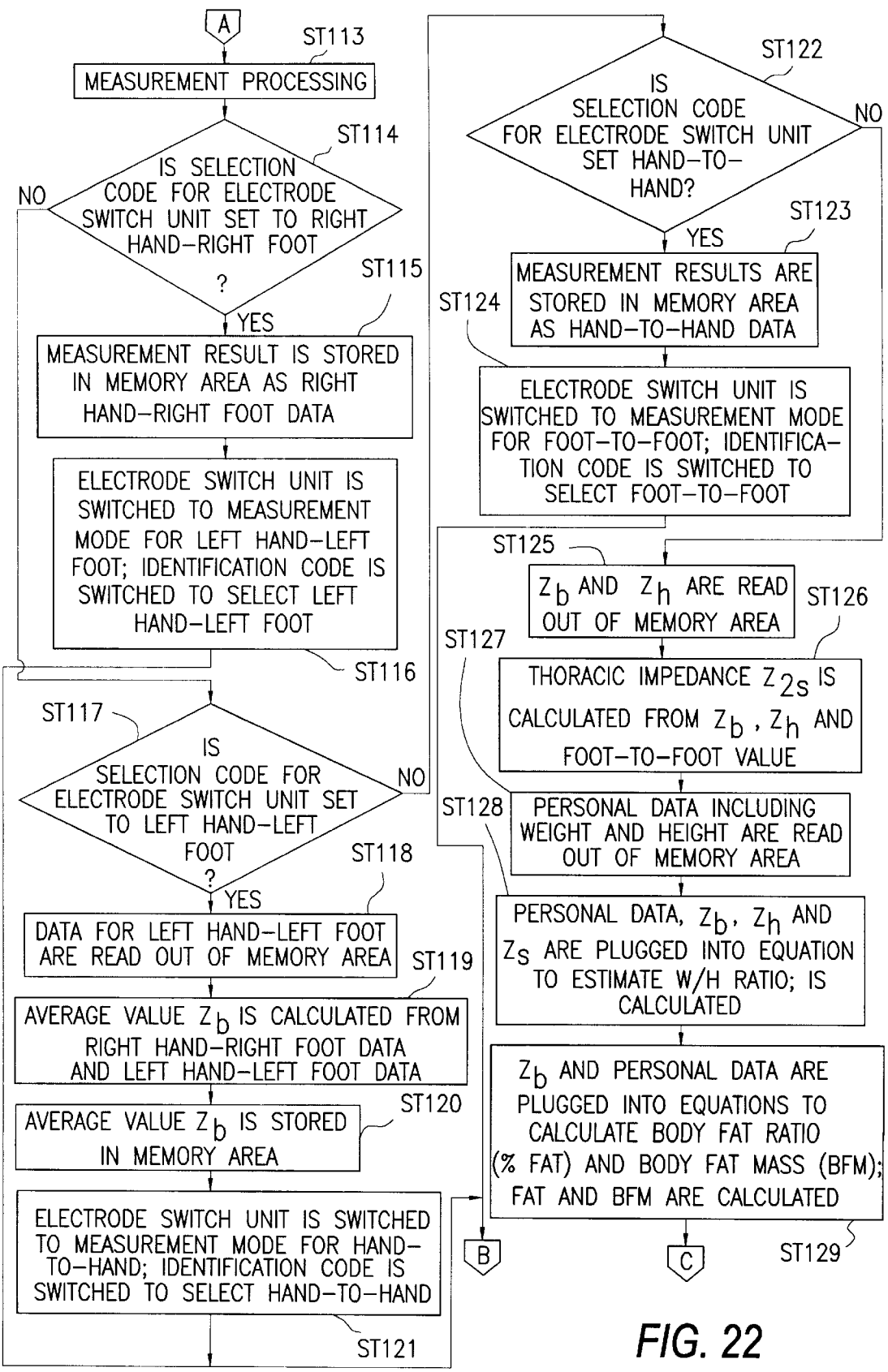
FIG. 22 is another flowchart of the measurement operations performed by the same device.
Figure 23:
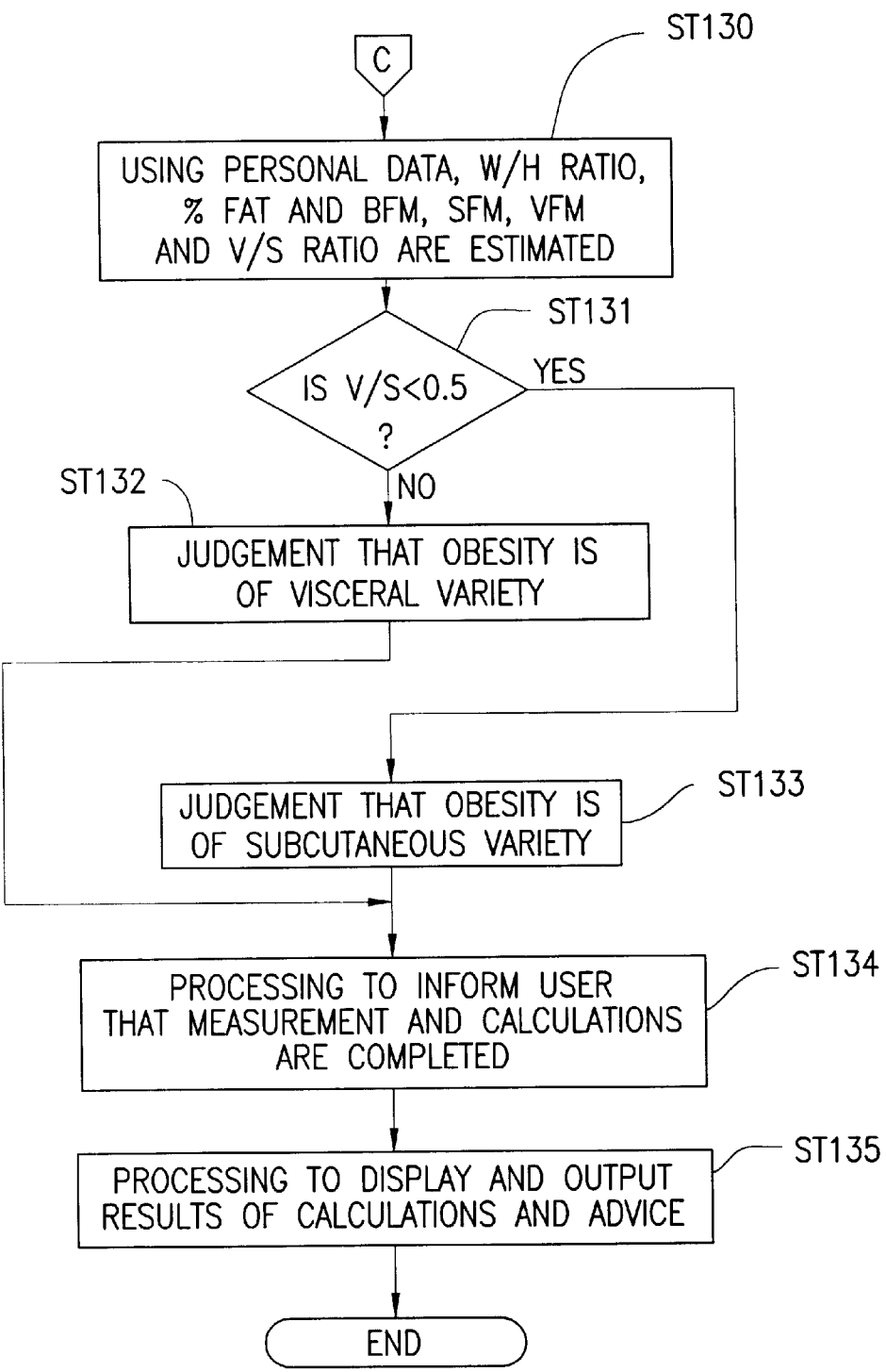
FIG. 23 is another flowchart of the measurement operations performed by the same device.
Figure 24:
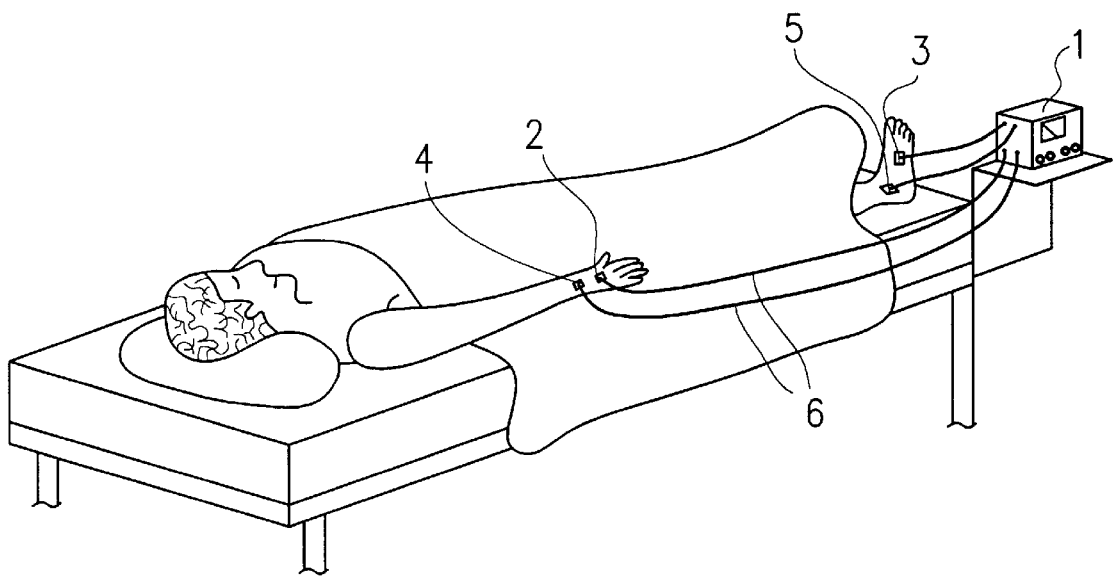
FIG. 24 illustrates how the impedance of the body was measured using a technique of the prior art.
Figure 25:
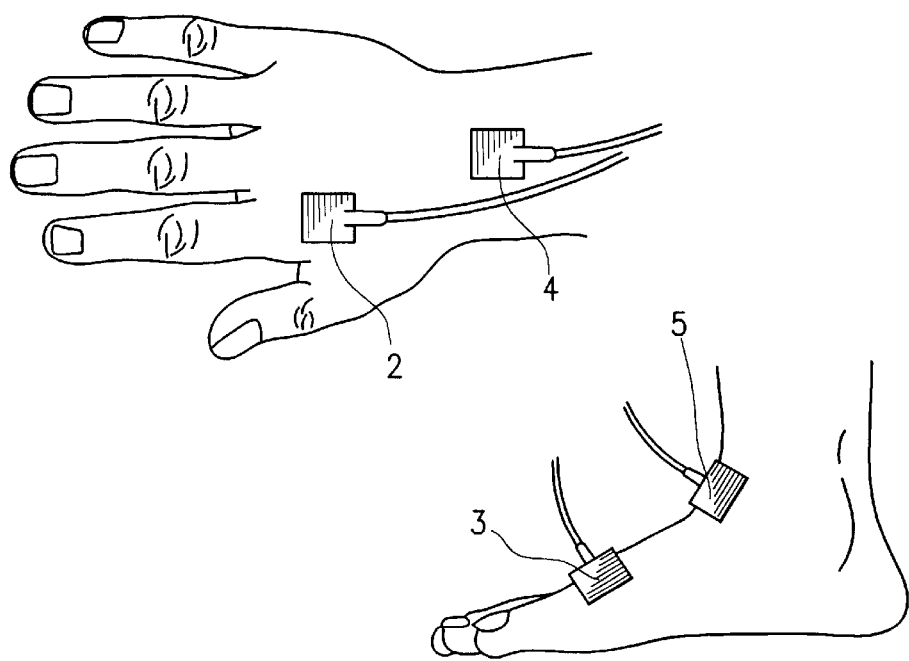
FIG. 25 shows the electrodes used on the patient's hand and foot when the impedance of the body was measured using a technique of the prior art.

The operation of this embodiment of the device will be explained with reference to the flowchart shown in FIGS. 21, 22 and 23.

Figure 13:
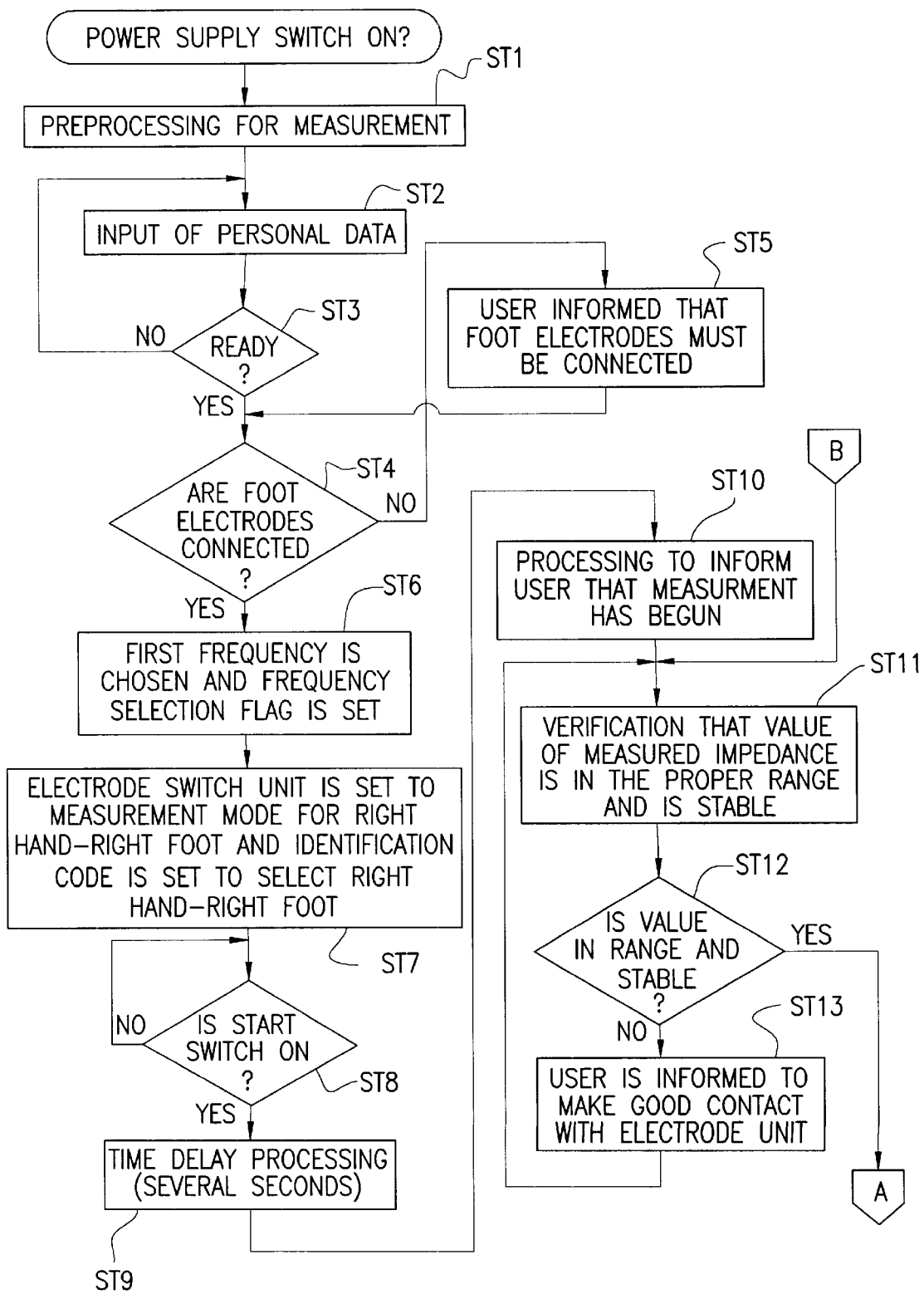
FIG. 13 is a flowchart of the operations performed when the same embodiment uses as its standard mode the measurement of the impedance between one hand and foot.
Figure 14:
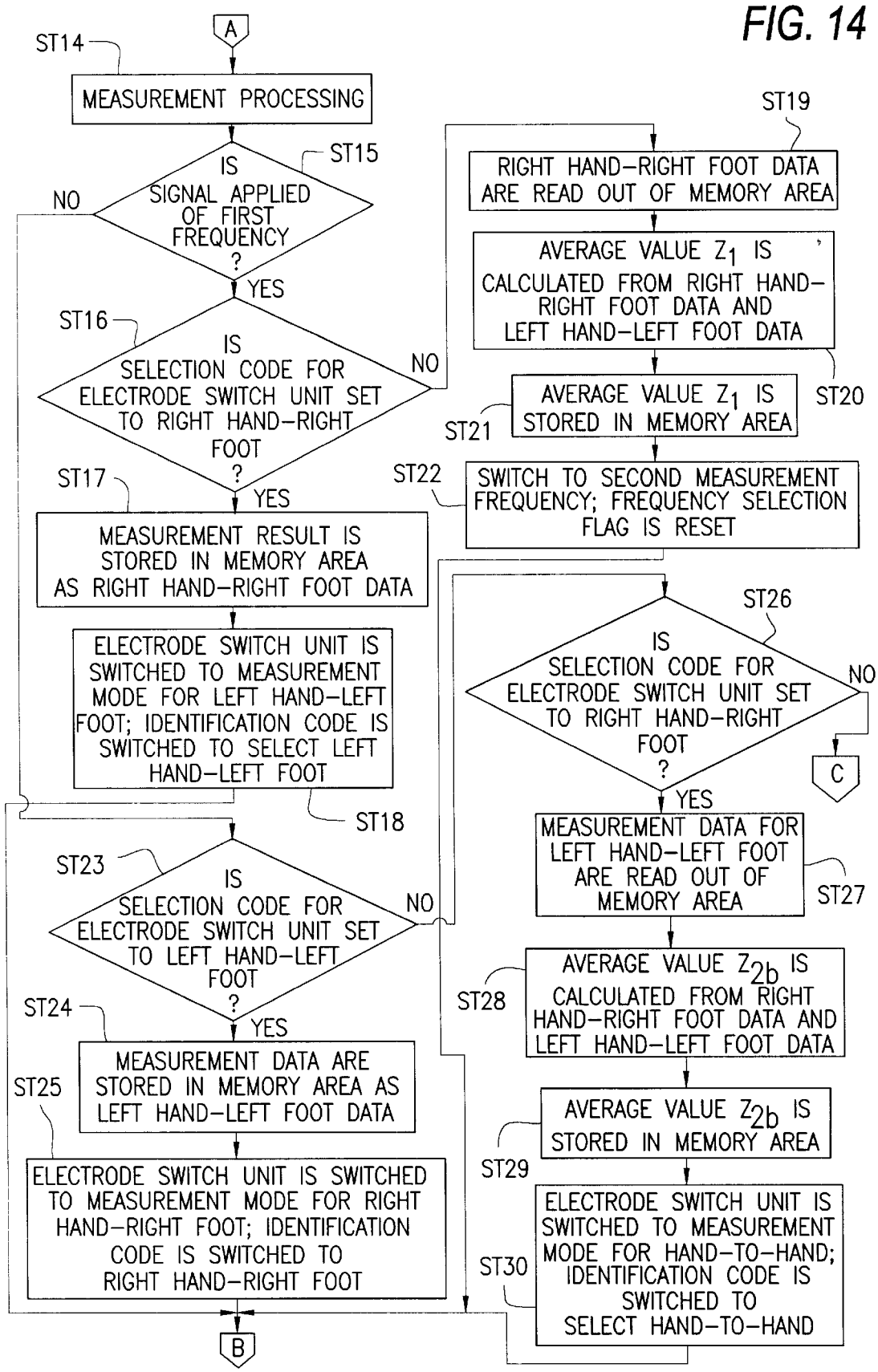
FIG. 14 is another flowchart of the operations performed by the same embodiment.
Figure 15:
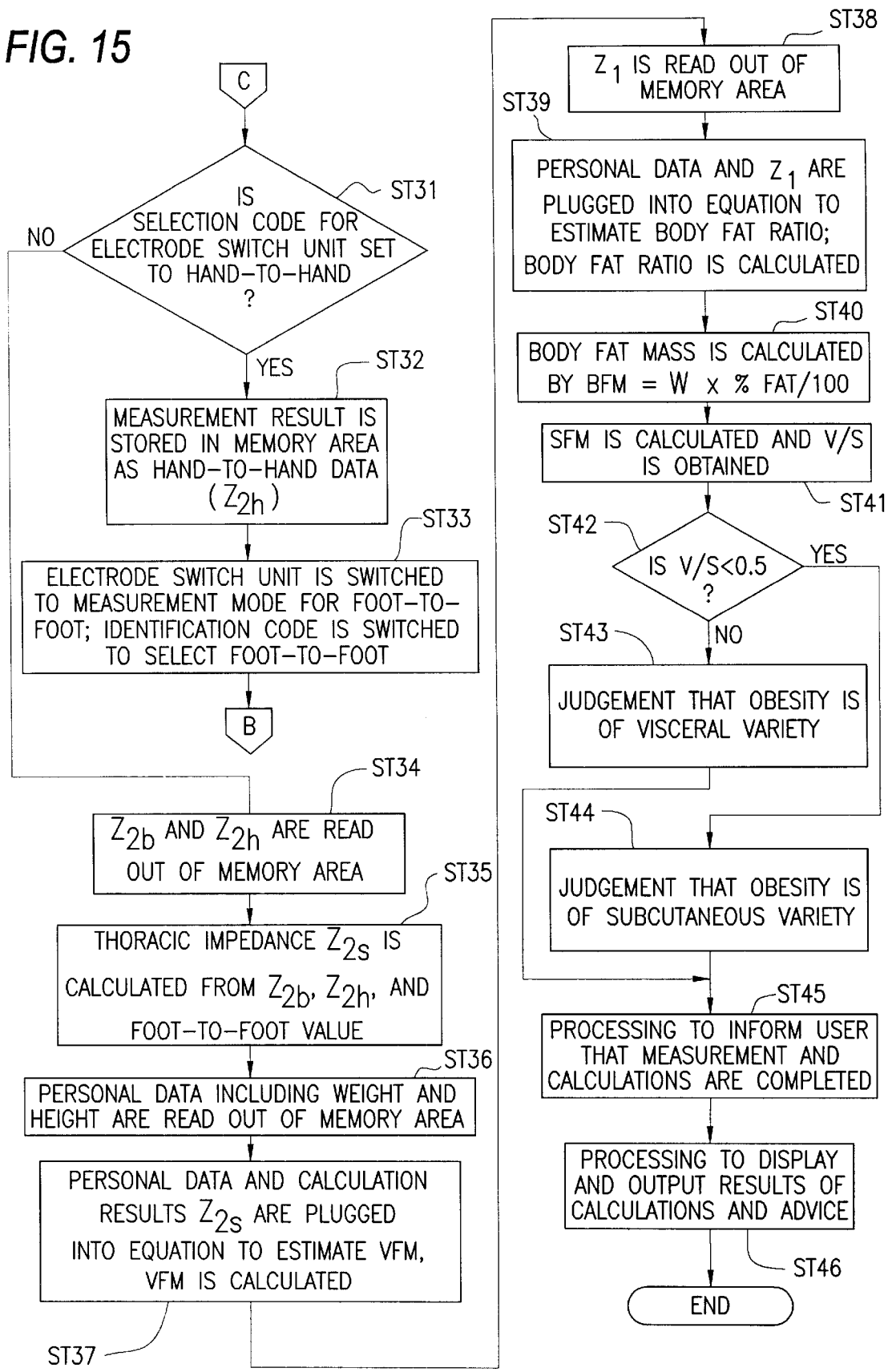
FIG. 15 is another flowchart of the operations performed by the same embodiment.

The initial power-up processing in ST 101 through 105 is the same as that in ST 1 through 5 in FIGS. 13 through 15. After ST 104 verifies that good contact is being made with the foot electrodes, electrode switch 32 is set to measurement mode for right hand-right foot, and the identification code is set to right hand-right foot (ST 106).

When the setting of the switches is completed, the device stands by until the start switch on input unit 15 is actuated (ST 107). When this switch is turned on, the time delay processing is performed (ST 108), and the user is informed that measurement has begun (ST 109). The impedance $Z_{Rh-Rf}$ between right hand and foot is measured in ST 110 through 113.

Next, the CPU determines whether the selection code for the electrode switch unit is set for right hand-right foot (ST 114). Since this determination will be "yes" at this time, the measurement result, i.e., the impedance value which was measured, will be stored in the memory area as right hand-right foot impedance $Z_{Rh-Rf}$ (ST 115), electrode switch unit 32 will be switched to left hand-left foot mode, and the identification code will be changed to select left hand-left foot (ST 116). Processing flow returns to ST 110, and the impedance $Z_{Lh-Lf}$ between the left hand and foot is measured in ST 110 through 113. The determination in ST 114, whether the selection code for the electrode switch unit is set for right hand-right foot, will now be "no", since the code was changed to left hand-left foot in ST 116, so flow proceeds to ST 117.

ST 117 makes a determination whether the selection code is set for left hand-left foot. Since the answer is now "yes", the impedance $Z_{Rh-Rf}$ between right hand and foot is read out of the memory area where it was stored (ST 118). Along with impedance $Z_{Lh-Lf}$ between left hand and foot, this value is used to calculate the average value $Z_b$ by solving $Z_b = (Z_{Rh-Rf} + Z_{Lh-Lf})/2$ (ST 119). This average value $Z_b$ is stored in the memory area (ST 120), the electrode switch unit is switched to hand-to-hand mode, the identification code is changed to select hand-to-hand (ST 121), and flow returns to ST 110.

The impedance $Z_h$ between the hands is measured in ST 110 to 113. Since the determination in ST 114 and 117 will be "no", flow proceeds to ST 122 which determines whether the selection code indicates hand-to-hand. Since the answer will be "yes", the measurement result, i.e., the impedance $Z_h$ measured between the hands, is stored in the memory area (ST 123). The electrode switch unit is switched to foot-to-foot measurement mode, the identification code is switched to foot-to-foot (ST 124), and program flow returns to ST 110.

The impedance $Z_f$ between the feet is measured in ST 110 to 113. Since the determinations in ST 114, 117 and 122 will all be "no", flow moves to ST 125, where the average impedance $Z_b$ between hands and feet and the impedance $Z_h$ between the hands is read out of the memory area. From impedance values $Z_b$, $Z_h$ and $Z_f$, the impedance between the feet, the impedance $Z_S$ of the thoracic region is obtained by solving $Z_S = Z_b - (Z_h + Z_f)/2$ (ST 126). Next, the personal data including weight and height are read out of the memory area (ST 127). By substituting these personal data and $Z_S$, $Z_h$ and $Z_f$ in the formula to estimate the W/H ratio, the ratio (ST 128) is obtained. And by substituting the average impedance $Z_b$ between hand and foot and the personal data in the formulas to estimate body fat ratio and body fat mass, % Fat and BFM (ST 129) are calculated. The personal data, W/H ratio, body fat ratio and BFM yield the following.

$$V/S = \frac{VFM}{SFM} = \alpha(W/H) + \beta \qquad \text{Formula 6.}$$

Here $\alpha$ and $\beta$ are constants. SFM and BFM are calculated by SFM=BFM/(1+V/S) and VFM=BFM−SFM. The visceral-to-subcutaneous ratio V/S, the subcutaneous fat mass SFM and the visceral fat mass VFM are calculated (ST 130).

Just as in ST 42 through 46 in FIGS. 13 through 15, a determination is made as to whether the V/S ratio is less than 0.5 (ST 131). If it is less, a determination is made that the obesity is of the subcutaneous type (ST 133). If the ratio exceeds 0.5, the obesity is judged to be of the visceral type (ST 132). When all measurements and calculations have been completed, display 16 and buzzer 29 indicate completion (ST 134). The results of the calculations and advisory data are displayed on display 16 or output to the exterior via a communication device (ST 135).

Although only a few embodiments have been described in detail above, those having ordinary skill in the art will certainly understand that many modifications are possible in the preferred embodiment without departing from the teachings thereof.

All such modifications are intended to be encompassed within the following claims.

What is claimed is:

1. A body fat detecting device, comprising:
   a first pair of electrodes and a second pair of electrodes;
   a main unit having first and second body contact elements at respective ends of the main unit, each of said first and second body contact elements including thereon an electrode from each of said first pair of electrodes and said second pair of electrodes;
   a signal generator configured to supply a high frequency signal to said first pair of electrodes;
   a determination device which determines an impedance between said second pair of electrodes;
   a calculating device which calculates fat data based on said impedance; and a display for displaying results calculated by said calculating device and located on said main unit.

2. A body fat detecting device according to claim 1 further comprising means for allowing entry of individual data about a subject, and wherein said calculating device is responsive to said individual data for calculating a fat mass.

3. A body fat detecting device according to claim 1 wherein said signal generator is configured to supply a first high frequency current, wherein said first high frequency current travels primarily towards external tissue, and a second high frequency current, wherein said second high frequency current travels primarily towards internal tissues.

4. A body fat detecting device according to claim 3 wherein said calculating device calculates a ratio between visceral fat mass and subcutaneous fat mass and uses said ratio to determine a type of fatness of the subject.

5. A body fat detecting device, comprising:
   a first pair of electrodes and a second pair of electrodes;
   a main unit having first and second body contact elements at respective ends thereof, each of said first and second body contact elements comprising an electrode from each of said first pair of electrodes and said second pair of electrodes;
   a signal generator configured to supply a high frequency signal to said first pair of electrodes;
   a determination device which determines an impedance between said second pair of electrodes;
   verification means for verifying if a value of said impedance is in a proper range and is stable;
   a calculating device which calculates fat data based on said impedance if said verification means verifies said value of said impedance is in a proper range and is stable; and
   a display for displaying results calculated by said calculating device and located on said main unit.

6. A body fat detecting device according to claim 5, wherein said body contact elements comprise top units at top ends of said main unit and bottom units at bottom ends of said main unit.

7. A body fat detecting device according to claim 5, wherein said means for determining an impedance comprises means for providing a time delay processing after a start key on said main unit is initiated in order to ensure that said body contact elements are properly contacted.

8. A body fat detecting device according to claim 7, further comprising means for allowing entry of individual data about a subject, and wherein said calculating means is responsive to said individual data for calculating a fat mass.

9. A body fat detecting device according to claim 7, wherein said signal generator comprises first means for supplying a first high frequency current, wherein said first high frequency current travels primarily towards external tissue, and second means for supplying a second high frequency current, wherein said second high frequency current travels primarily towards internal tissue.

10. A body fat detecting device according to claim 7, wherein said calculating device calculates a ratio between visceral fat mass and subcutaneous fat mass and uses said ratio to determine a type of obesity.

11. A body fat detecting device, comprising:
    a first pair of electrodes and a second pair of electrodes;
    a main unit having first and second body contact elements at respective ends thereof, each of said first and second body contact elements comprising an electrode from each of said first pair of electrodes and said second pair of electrodes;
    a signal generator configured to supply a high frequency signal to said first pair of electrodes;
    a determination device which determines an impedance between said second pair of electrodes;
    verification means for verifying if a value of said impedance is in a proper range and is stable in order to ensure that said first and second body contact elements are properly engaged;
    a calculating device which calculates a fat mass based on said impedance if said verification means verifies said value of said impedance is in a proper range and is stable; and
    a display for displaying results calculated by said calculating device and located on said main unit.

* * * * *